US007253159B2

(12) United States Patent
Moody et al.

(10) Patent No.: US 7,253,159 B2
(45) Date of Patent: Aug. 7, 2007

(54) METHODS AND COMPOSITIONS FOR IMMUNOMODULATION USING CD1 ANTIGENS

(75) Inventors: D. Branch Moody, West Roxbury, MA (US); David C. Young, Benton, ME (US); Catherine E. Costello, Reading, MA (US)

(73) Assignees: The Brigham and Women's Hospital, Inc., Boston, MA (US); Trustees of Boston University, Boston, MA (US)

( * ) Notice: Subject to any disclaimer, the term of this patent is extended or adjusted under 35 U.S.C. 154(b) by 32 days.

(21) Appl. No.: 10/827,616

(22) Filed: Apr. 19, 2004

(65) Prior Publication Data

US 2004/0265976 A1 Dec. 30, 2004

Related U.S. Application Data

(60) Provisional application No. 60/464,228, filed on Apr. 18, 2003.

(51) Int. Cl.
C07D 405/12 (2006.01)
A61K 31/55 (2006.01)
(52) U.S. Cl. ............................ 514/212.08; 540/524
(58) Field of Classification Search .............. 540/524; 514/212.08
See application file for complete search history.

(56) References Cited

U.S. PATENT DOCUMENTS

| 5,538,733 | A | 7/1996 | Emery et al. |
| 5,679,347 | A | 10/1997 | Porcelli et al. |
| 5,853,737 | A | 12/1998 | Modlin et al. |
| 6,063,919 | A | 5/2000 | Gaudioso et al. |
| 6,238,676 | B1 | 5/2001 | Porcelli et al. |
| 6,310,058 | B1 | 10/2001 | Miller et al. |
| 2002/0009465 | A1 | 1/2002 | Porcelli et al. |
| 2003/0206914 | A1 | 11/2003 | Porcelli et al. |

FOREIGN PATENT DOCUMENTS

| WO | WO 95/00163 A1 | 1/1995 |
| WO | WO 96/12190 A2 | 4/1996 |
| WO | WO 99/12562 A1 | 3/1999 |
| WO | WO 99/52547 A1 | 10/1999 |
| WO | WO 03/013596 A | 2/2003 |

OTHER PUBLICATIONS

Tsukamoto et al. (Journal of Antibiotics (1997), 50(10), 815-821).*
Ikeda-Fujita, T. et al., "Antitimor Effects of a Novel Immunomodulator Holding Many Bioactivitiesw in Common With Endotoxins Derived From Mycobacteriam-Bovis BCG", *Japanese J. of Bacteriology*, vol. 42(6), pp. 851-856, 1987.
Adilakshmi et al., Mutational analysis of a role for salicylic acid in iron metabolism of *Mycobacterium smegmatis*. J Bacteriol. Jan. 2000;182(2):264-71.
Bosne-David et al., Evaluation of growth promotion and inhibition from mycobactins and nonmycobacterial siderophores (Desferrioxamine and FR160) in *Mycobacterium aurum*. Antimicrob Agents Chemother. Aug. 1997;41(8):1837-9.
Cui et al., Requirement for Valpha 14 NKT cells in IL-12-mediated rejection of tumors. Science. Nov. 28, 1997;278(5343):1623-6.
DeVoss et al., The salicylate-derived mycobactin siderophores of Mycobacterium tuberculosis are essential for growth in macrophages. Proc Natl Acad Sci U S A. Feb. 1, 2000;97(3):1252-7.
Dussurget et al., An ideR mutant of *Mycobacterium smegamatis* has derepressed siderophore production and an altered oxidative-stress response. Mol Microbiol. Nov. 1996;22(3):535-44. Abstract Only.
Fiss et al., Identification of genes involved in the sequestration of iron in mycobacteria: the ferric exochelin biosynthetic and uptake pathways. Mol Microbiol. Nov. 1994;14(3):557-69. Abstract Only.
Gobin et al., Exochelins of *Mycobacterium tuberculosis* remove iron from human iron-binding proteins and donate iron to mycobactins in the M. tuberculosis cell wall. J Exp Med. Apr. 1, 1996;183(4):1527-32.
Gobin et al., Iron acquisition by *Mycobacterium tuberculosis*: isolation and characterizationi of a family of iron-binding exochelins. Proc Natl Acad Sci U S A. May 23, 1995;92(11):5189-93.
Lambrecht et al., Inability to detect mycobactin in mycobacteria-infected tissues suggests an alternative iron acquisition mechanism by mycobacteria in vivo. Microb Pathog. Mar. 1993;14(3):229-38. Abstract Only.
Lin et al., The remarkable hydrophobic effect of a fatty acid side chain on the mirobial growth promoting activity of synthetic siderophore. Biometals. Jun. 2001;14(2):153-7. Abstract only.
Matzanke et al., Iron uptake and intracellular metal transfer in mycobacteria mediated by xenosiderophores. Biometals. Jul. 1997;10(3):193-203. Abstract Only.
Messenger et al., Iron uptake processes in Mycobacterium vaccae R877R, a mycobacterium lacking mycobactin. J Gen Microbiol. Mar. 1986;132 (Pt 3):845-52. Abstract Only.
Moody et al., T cell activation by lipopeptide antigens. Science. Jan. 23, 2004;303(5657):527-31.
Moody Cliffe et al., Immune suppression and skin cancer development: regulation by NKT cells. Nat Immunol. Dec. 2000;1(6):521-5.
Nieuwenhuis et al., CD1d-dependent macrophage-mediated clearance of *Pseudomonas aeruginosa* from lung. Nat Med. Jun. 2002;8(6):588-93.
Quadri et al., Identification of a *Mycobacterium tuberculosis* gene cluster encoding the biosynthetic enzymes for assembly of the virulence-conferrring siderophore mycobactin. Chem Biol. Nov. 1998;5(11):631-45.
Raghu et al., Effect of anti-tuberculosis drugs on the iron-sequestration mechanisms of mycobacteria. Indian J Pathol Microbiol. Jul. 1995;38(3):287-92. Abstract Only.

(Continued)

*Primary Examiner*—Bruck Kifle
(74) *Attorney, Agent, or Firm*—Wolf, Greenfield & Sacks, P.C.

(57) ABSTRACT

The invention relates to novel CD1*a*-presented antigens. These antigens can be used as antigens, adjuvants or as immunomodulatory agents in a variety of diagnostic, therapeutic and prophylactic applications.

32 Claims, 9 Drawing Sheets

OTHER PUBLICATIONS

Raghu et al., Effect of iron on the growth and siderophore production of mycobacteria. Biochem Mol Biol Int. Oct. 1993;31(2):341-8. Abstract Only.

Raghu et al., Isolation and characterization of siderophores and envelope proteins from mycobacteria. Biochem Mol Biol Int. Oct. 1993;31(2):333-9. Abstract Only.

Raghu et al., Effect of hemoglobin on the growth of mycobacteria and the production of siderophores. Indian J Pathol Microbiol. Oct. 1993;36(4):376-82. Abstract Only.

Ratledge et al., The occurrence of carboxymycobactin, the siderophore of pathogenic mycobacteria, as a second extracellular siderophore in *Mycobacterium smegmatis*. Microbiology. Aug. 1996;142 (Pt 8):2207-12. Abstract Only.

Rosat et al., CD1-restricted microbial lipid antigen-specific recognition found in the CD8+ alpha beta T cell pool. J Immunol. Jan. 1, 1999;162(1):366-71.

Scheibel et al., Antimalarial activity of selected aromatic chelators. IV. Cation uptake by Plasmodium falciparum in the presence of oxines and siderochromes. Mol Pharmacol. Oct. 1986;30(4):364-9. Abstract Only.

Schumann et al., Screening system for xenosiderophores as potential drug delivery agents in mycobacteria. Antimicrob Agents Chemother. May 2001;45(5):1317-22.

Snow et al., Metal complexes of mycobactin P and of desferrisideramines. Biochem J. Nov. 1969;115(2):199-205.

Stenger et al., Differential effects of cytolytic T cell subsets on intracellular infection. Science. Jun. 13, 1997;276(5319):1684-7.

Szarapinska-Kwaszewska et al., [Utilization of siderophores from mycobacteria by *Staphylococcus*] Med Dosw Mikrobiol. 1998;50(3-4):239-49. Polish.

Terabe et al., NKT cell-mediated repression of tumor immunosurveillance by IL-13 and the IL-4R-STAT6 pathway. Nat Immunol. Dec. 2000;1(6):515-20.

Zhu et al., Exochelin genes in *Mycobacterium smegmatis*: identification of an ABC transporter and two non-ribosomal peptide synthetase genes. Mol Microbiol. Jul. 1998;29(2):629-39.

Vergne et al., Iron chelators from mycobacteria (1954-1999) and potential therapeutic applications, *Nat. Prod. Rep.*, 2000, 17:99-116.

\* cited by examiner

METHODS AND COMPOSITIONS FOR IMMUNOMODULATION USING CD1 ANTIGENS

RELATED APPLICATIONS

This application claims priority to U.S. Provisional Patent Applications filed Apr. 18, 2003, entitled "METHODS AND COMPOSITIONS FOR IMMUNOMODULATION USING CD1 ANTIGENS", Ser. No. 60/464,228, the contents of which are incorporated by reference herein in their entirety.

GOVERNMENT SUPPORT

Aspects of the invention may have been made using funding from National Institutes of Health Grants AI49313, RR10888 and RR10493. Accordingly, the Government may have rights in the invention.

FIELD OF THE INVENTION

The invention relates to immunomodulation using CD1-presented antigens, and particularly CD1a-presented antigens.

BACKGROUND OF THE INVENTION

The immune system is a complex system of molecular and cellular defenses that recognize potentially harmful exogenously or endogenously derived antigens. When stimulated, the immune system undergoes a series of activities that results in an immune response that is cell-mediated, antibody-mediated (i.e., humoral), or a combination of both.

A large part of the cell-mediated immune response is the activation of T cells through the recognition of and response to antigen presentation. It has long been recognized that antigens derived from polypeptides are presented to T cells through a group of molecules known as major histocompatibility complex (MHC) molecules. In MHC-mediated presentation, the T cell antigen receptor recognizes a peptide in combination with an MHC molecule. In general, antigens presented by MHC class I molecules are recognized by $CD8^+$ T cells, while antigens presented by MHC class II molecules are recognized by $CD4^+$ T cells. See, for instance, the description of MHC molecules and their antigen presentation in U.S. Pat. Nos. 5,679,347; 5,853,737 and 6,238,676.

Recently, it has also been recognized that antigen presentation occurs through a distinct family of antigen presenting molecules, CD1 molecules. In humans, five CD1 genes have been identified: CD1a, CD1b, CD1c, CD1d and CD1e. These proteins are displayed on antigen presenting cells which include Langerhans cells, activated B-cells, dendritic cells in lymph nodes, activated blood monocytes, etc. Although there is a structural resemblance to MHC molecules, CD1 molecules differ from MHC molecules in a variety of ways. For instance, CD1 genes are apparently non-polymorphic, while human MHC genes are highly polymorphic. Additionally, until the instant invention, CD1 molecules were believed capable of presenting only non-peptide antigens, unlike MHC molecules.

Responses to non-peptide antigens have been previously reported. For example, $CD4^- CD8^-$ and $CD8^+$ T cells expressing αβ T cell receptors (TCRs) recognized *M. tuberculosis* lipid and lipoglycan antigens presented by CD1b proteins and, as a result, exhibited measurable proliferation and interferon-γ secretion (Porcelli et al. Nature 1992, 360(6404):593-7; Stenger, S., et al., Science 276:1684-1687 (1996)). In another study, two $CD8^+$ TCR αβ$^+$ T cell lines displayed cytotoxicity and strong Th cell type I cytokine response as a result of the recognition of *M. tuberculosis* antigens when presented by CD1a or CD1c proteins (Rosat et al., Journal of Immunology 162:366-371 (1999)).

Beyond being involved in the response of the immune system to bacterial invasion, CD1-presentation may also play a role in autoimmune disease. CD1 molecules have been shown to be recognized by $CD4^- CD8^-$ T cells derived from patients with SLE (Porcelli, et al., Nature 341:447-450 (1989)), and even though no foreign antigen was present, leukemia cells expressing CD1 molecules were lysed by the T cells. More recent studies have shown that self lipids like phosphatidylinositols, gangliosides and sulfatides can lead to T cell activation in vitro and in human disease. (Shamshiev et al. Eur J Immunol. 1999, 29(5):1667-75; Gumperz et al. Immunity. 2000 February;12(2):211-21.) In addition, CD1d proteins have been shown to modulate T cell responses to tumors in ways that affect the final outcome of immune mediated diseases (Moodycliffe et al. 2000, Nat. Immunol. 1:521-525; Terabe et al. Nat Immunol. 2000, 1(6):515-20; and Cui et al. Science, 1997, 278(5343):1626-9.)

Due to the involvement of CD1 presentation in stimulating T cell responses, new CD1-presented antigens would be useful in augmenting and/or polarizing immune responses. These antigens would therefore be useful in detecting and treating microbial (e.g., bacterial) infections, autoimmune diseases or other diseases in which T cells play a role.

SUMMARY OF THE INVENTION

The invention relates to the identification of CD1-presented antigens, and more particularly CD1a-presented antigens. Compositions and methods relating to these antigens are provided, as are inter alia methods of identifying further CD1a-presented antigens and blocking agents that interfere with presentation of such antigens, detection of conditions (e.g., infections) associated with the CD1a-presented antigens of the invention, and/or activation of T cells that recognize the antigens.

In their broadest sense, the antigens of the invention are or comprise lysine or cysteine acylated peptides. The lysine acylated peptides comprise any amino acid sequence with an epsilon lysine acylation.

The antigens of the invention may have the structure of Formula I

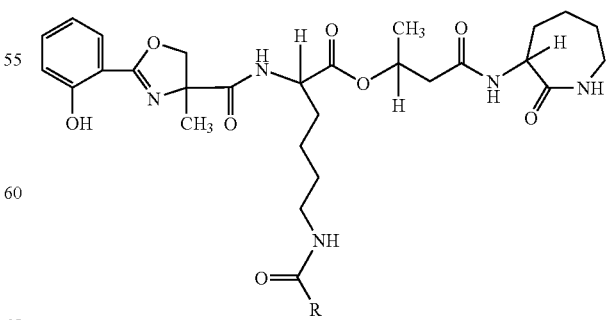

wherein R is an alkyl chain or an alkene chain, or

Formula II

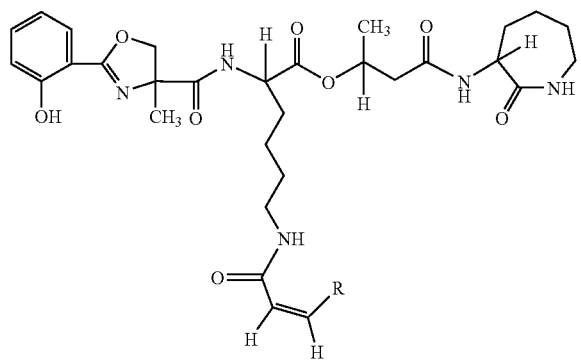

wherein R is an alkyl chain or an alkene chain, or Formula III

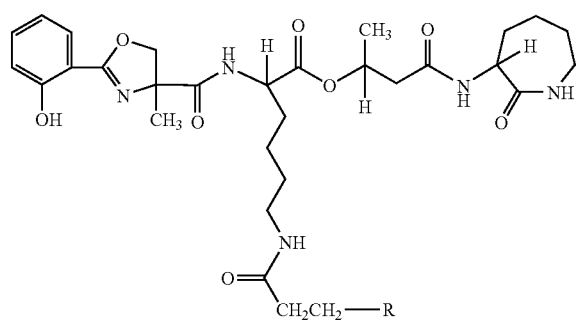

wherein R is an alkyl chain or an alkene chain.

The antigen may be more specifically an antigen having the structure of or an antigen having the structure of

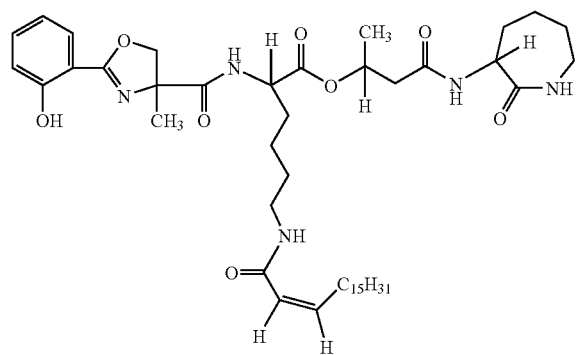

or an antigen having the structure of or an antigen having the structure of

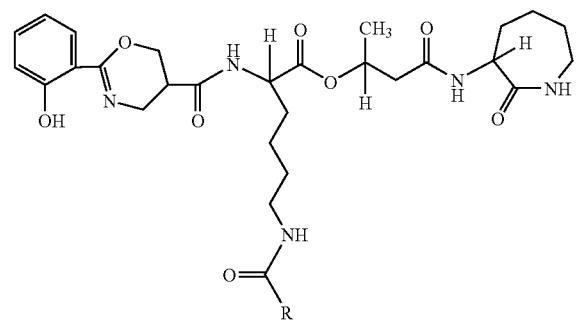

The antigen may also be an antigen having a structure of Formula IV wherein R is an alkyl chain or an alkene chain, or Formula V wherein R is an alkyl chain or an alkene chain, or Formula VI

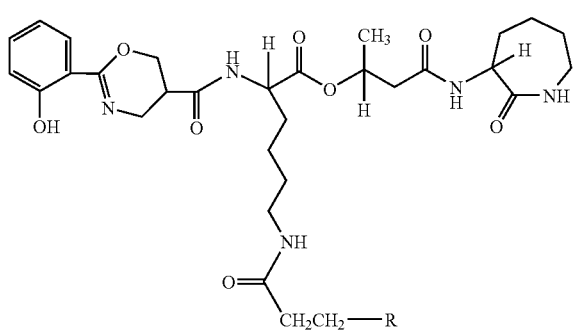

wherein R is an alkyl chain or an alkene chain.

The antigen may be more specifically an antigen having the structure of

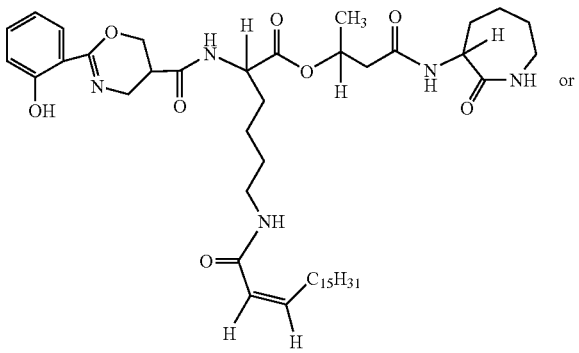

or

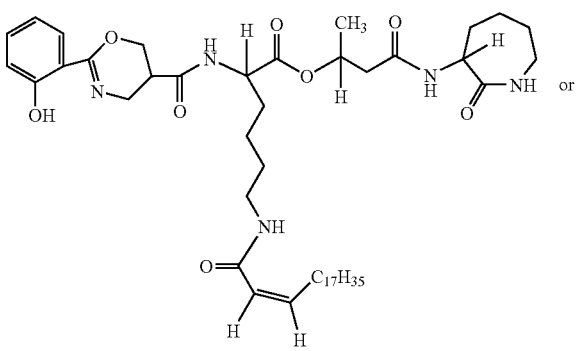

or

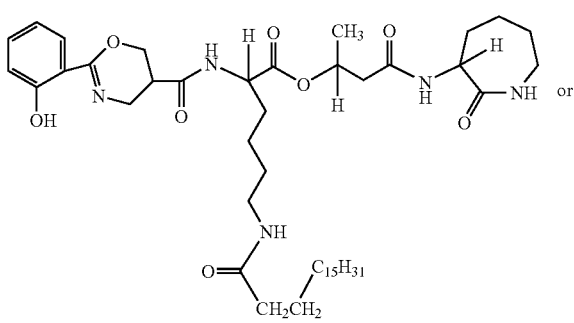

or

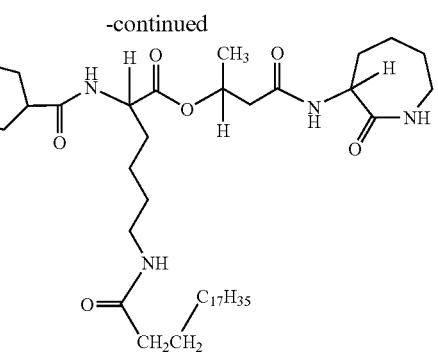

The antigens of the invention may comprise an R group that is $C_{15}H_{31}$ or $C_{17}H_{35}$, but are not so limited. The R may be at least 12, at least 13, at least 14, at least 15, at least 16, at least 17 or at least 18 carbons in length, in some embodiments. In related embodiments, R is selected from the group consisting of alkyls or alkenes such as but not limited to C20, C20:1, C19, C19:1, C18, C18:1, C17, C17:1, C16, C16:1, C15, C15:1, C14, C14:1, C13, C13:1, C12 and C12:1. In some important embodiments, R is an unsaturated alkyl. R may comprise one, two, three or more double bonds. Thus the antigens of the invention include but are not limited to DDM838, DDM840, DDM810, DDM812, DDM838-threonine, DDM840-threonine, DDM810-threonine and DDM812-threonine.

Unless otherwise indicated, the following aspects relate equally to the antigens provided above. Thus, in some aspects of the invention all the afore-mentioned antigens can be employed while in others DDM838 and DDM810 are most preferred. Some aspect employ DDM840 also, while others preferably do not employ DDM812.

In one aspect, the invention provides a composition comprising an isolated antigen, wherein the antigen is any of the foregoing antigens. The composition may further comprise a pharmaceutically acceptable carrier, in which case it may be referred to as a pharmaceutical composition or a pharmaceutical preparation. The antigen may be present in an amount effective to induce an immune response, such as a CD1 immune response.

The composition may further comprise an immunomodulatory agent. In one embodiment, the immunomodulatory agent is an adjuvant or a cytokine. The adjuvant may also be selected from the group consisting of Freund's adjuvant and mycobacterial cell wall lipids. In one embodiment, the cytokine is IL-4 or GM-CSF.

In one embodiment, the composition further comprises a non-CD1-presented antigen, such as but not limited to an MHC-presented antigen.

In other embodiments, the antigen is present on a CD1a-expressing cell such as a CD1a-expressing dendritic cell. The CD1a-expressing cell may be a cell that naturally expresses CD1a, a cell that is induced to express CD1a, for example, by culture in GM-CSF and/or IL-4, or it may be a transfectant (i.e., a cell into which an exogenous nucleic acid is introduced and from which CD1a is expressed).

In another aspect, the invention provides compositions, and preferably pharmaceutical compositions (as defined herein), that comprise a substantially pure composition of one antigen of the invention. These compositions may have various embodiments, including those recited herein for compositions of isolated antigen.

In another aspect, the invention provides a method for producing an antigen of Formula I comprising performing a cold acetone precipitation of a mycobacterial sample to form a precipitate, dissolving the precipitate in chloroform, eluting the dissolved precipitate through a silica gel in a methanol solvent, and performing a reversed phase HPLC using C8 matrix.

In one embodiment, the mycobacterial sample is a *M. tuberculosis* sample. The mycobacterial sample may comprise mycobacteria grown in iron-free media. The mycobacterial sample may additionally or alternatively comprise mycobacteria incapable of DDM hydroxylation. Mycobacteria incapable of DDM hydroxylation lack the MbtG gene, in some embodiments. In still other embodiments, the mycobacterial sample comprises mycobacteria that are genetically engineered to overproduce mycobactin-like compounds. The mycobacteria that are genetically engineered may be mutated at the IdeR locus such that the level of IdeR gene product is reduced or eliminated completely (e.g., IdeR null mutants). In another embodiment, the mycobacteria that are genetically engineered are mutated at loci that encode iron-binding repressors of mycobactin synthesis.

In another aspect, the invention provides a method for inducing an immune response comprising administering to a subject in need thereof an antigen of the invention in an amount effective to induce a CD1 immune response. In one embodiment, the antigen preferably does not have a Formula III structure and/or is not DDM812.

In one embodiment, the subject has or is at risk of developing an infection, which may be a bacterial infection, a viral infection, a fungal infection, a parasitic infection, or a mycobacterial infection, but it is not so limited. The subject may be immunocompromised. In still other embodiments, the subject is undergoing surgery or will undergo surgery.

In another embodiment, the method further comprises administering to the subject an immunomodulatory agent that may be but is not limited to an adjuvant or a cytokine. The adjuvant may be Freund's adjuvant or mycobacterial cell wall lipids. The cytokine may be selected from the group consisting of IL-4 and GM-CSF.

According to some embodiments, the antigen is present on a CD1a-expressing cell such as a CD1a-expressing dendritic cell or a CD1a-transfected antigen presenting cell.

In still another aspect, the invention provides a method for inducing an immune response comprising administering to a subject in need thereof a dendritic cell and an antigen of the invention. The antigen may be bound to a CD1a on the surface of the dendritic cell. The dendritic cell may be a Langerhans cell. The antigen may be present on a CD1a-expressing dendritic cell. The dendritic cell may naturally express CD1a or it may be induced to express CD1a by culture in IL-4 and/or GM-CSF and/or by transfection.

The subject may have an infection or be at risk of developing an infection, such as a mycobacterial infection, a bacterial infection, a viral infection, a fungal infection, or a parasitic infection. The subject may be immunocompromised, or may be undergoing surgery or scheduled to undergo surgery.

The method may further comprise administering to the subject an immunomodulatory agent that may be but is not limited to an adjuvant and a cytokine. The adjuvant may be Freund's adjuvant and mycobacterial cell wall lipids, but is not so limited. The cytokine may be IL-4 and GM-CSF, but is not so limited.

In yet another aspect, the invention provides a method for identifying a CD1a-restricted antigen comprising contacting a CD1a protein with an isolated CD1a-restricted antigen in the presence and absence of a test compound, wherein a control level of binding between the CD1a protein and the isolated CD1a-restricted antigen is determined in the absence of the test compound and a test level of binding between the CD1a protein and the isolated CD1a-restricted antigen is determined in the presence of the test compound, and wherein a test level of binding that is less than a control level of binding indicates that the test compound is a CD1a-restricted antigen.

The isolated CD1a-restricted antigen may have a structure of Formula I, Formula II, Formula III, Formula IV, Formula V or Formula VI, wherein R is selected from the group consisting of an alkyl chain or an alkene chain. R may be $C_{15}H_{31}$ or $C_{17}H_{35}$. In some embodiments, R is at least 12, at least 13, at least 14, at least 15, at least 16, at least 17 or at least 18 carbons in length. In related embodiments, R is selected from the group consisting of alkyls or alkenes such as but not limited to C20, C20:1, C19, C19:1, C18, C18:1, C17, C17:1, C16, C16:1, C15, C15:1, C14, C14:1, C13, C13:1, C12 and C12:1. R may also be an unsaturated alkyl. In some embodiments, R comprises at least one, two or three double bond. In other embodiments, R is a saturated alkyl and is C17 or greater.

In some embodiments, the CD1a protein is isolated. The CD1a protein may be soluble. Alternatively, the CD1a protein may be cell-bound. In a related embodiment, the CD1a protein is provided as CD1a-expressing cell, such as a CD1a-expressing dendritic cell.

The method may further comprise stimulating T cells with the test compound.

In another aspect, the invention provides a method for detecting or diagnosing a condition associated with the CD1a-presented antigen of the invention. In some embodiments, the condition is an infectious disease such as a mycobacterial infection, a bacterial infection, a viral infection, a fungal infection or a parasitic infection. The method involves detecting a sample from a subject with an agent that binds to a CD1a-presented antigen of the invention, although the CD1a-presented antigen need not be in a complex with CD1a in order to be recognized and/or bound by the agent. Thus, the agent may bind to one of the antigens of the invention when that antigen is in soluble form. In one embodiment, the agent is an antibody or a fragment thereof. The method optionally further comprises comparing the level of binding of the agent to the sample with a control which can be a negative or a positive control or both.

In still another aspect, the invention provides antibodies and antibody fragments that bind to the antigens of the invention.

These and other aspects and embodiments will be described in greater detail herein.

BRIEF DESCRIPTION OF THE FIGURES

FIG. 1 shows the chemical structures of Formulae I, II or III antigens.

FIG. 2 shows the chemical structures of antigens DDM810, DDM838, DDM812 and DDM840.

FIG. 3 shows the chemical structures of Formulae IV, V and VI antigens.

FIG. 4 shows the chemical structures of antigens DDM810-threonine, DDM838-threonine, DDM812-threonine and DDM840-threonine.

FIG. 5 is a graph showing the positive ion mode electrospray ionization mass spectrum (MS/MS) of *M. tuberculosis* DDM838.

FIG. 6 is a graph showing the results of an activation assay of J.RT-3 T lymphoblastoid cells in response to *M. tuberculosis* lipid fractions that contain DDM838.

DETAILED DESCRIPTION OF THE INVENTION

Figure 1:
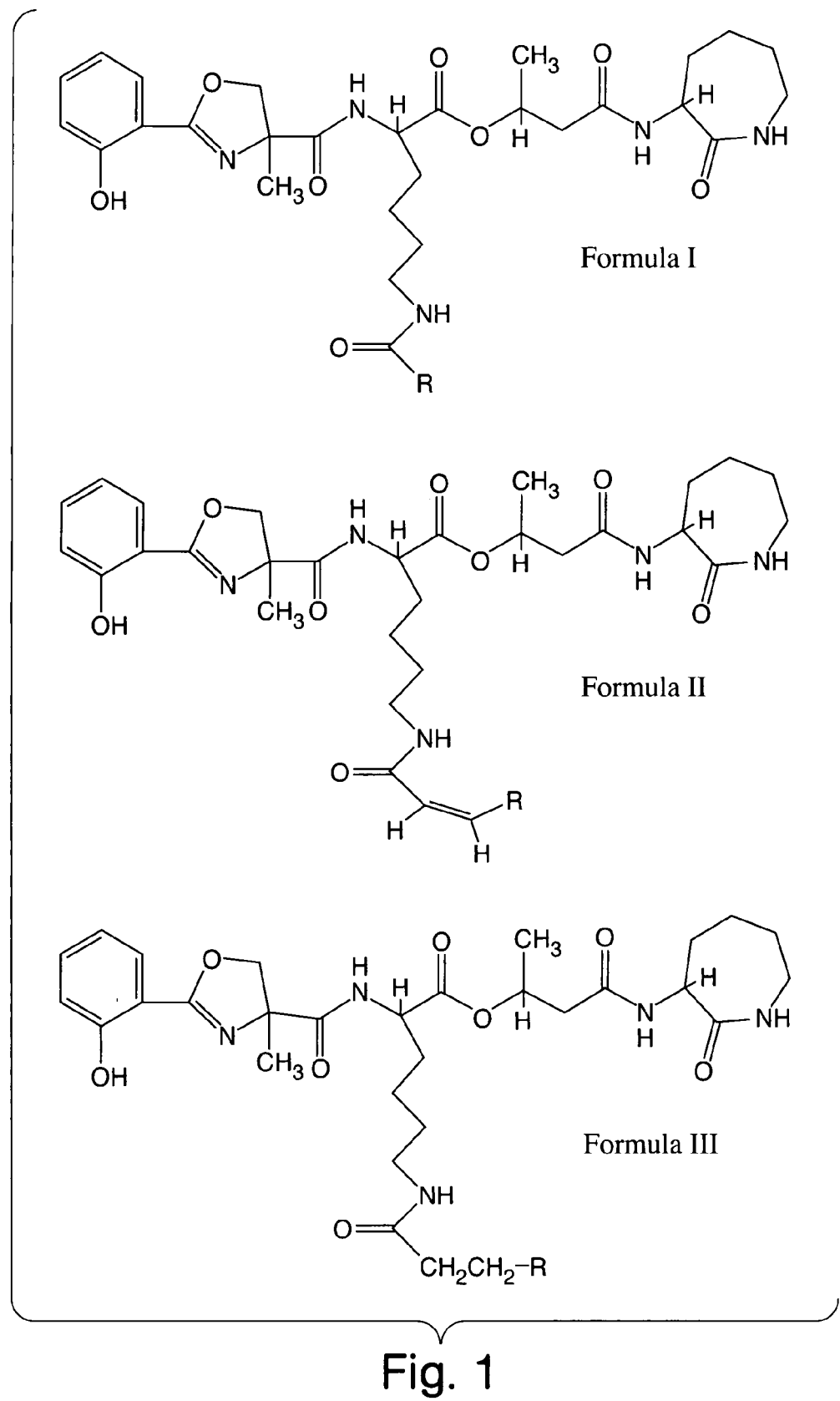

The invention is premised, in part, on the discovery of new antigens that are recognized by CD1 molecules. As used herein, an "antigen" is a molecule or composition of matter which induces an immune response in an animal, preferably a T cell or B cell immune response. A "foreign antigen" is an antigen that is not endogenously derived from a normal, healthy animal. In an unhealthy animal, endogenous molecules or compositions of matter that are expressed as a result of a condition or disease (e.g., cancer, etc.) can be recognized by the immune system as being foreign. Antigens also include "autoimmune antigens" which are normal, endogenously derived molecules or compositions of matter in an otherwise normal, healthy animal. Autoimmune antigens are also commonly referred to as "self antigens" or "autoantigens".

CD1 molecules are known to present non-peptide antigens such as lipids and glycolipids. These molecules are recognized by T cell clones (e.g., CD4$^-$CD8$^-$ clones) that express either α:β or γ:δ TCRs (Porcelli, S., et al., Nature 341:447-450 (1989); Faure, F., et al., Eur. J. Immun. 20:703-706 (1990)). Because of the structural resemblance of CD1 molecules, encoded by genes on human chromosome 1, to MHC molecules, encoded by genes on human chromosome 6 (Calabi, F. and Milstein, C., Nature 323:540-543 (1986); Balk, S. P., et al., Proc. Natl. Acad. Sci. USA 86:252-256 (1989)), it has been suggested that CD1 may represent a family of antigen presenting molecules separate from those encoded by the MHC genes (Porcelli, S., et al., Nature 341:447-450 (1989); Strominger, J. L., Cell 57:895-898 (1989); Porcelli, S., et al., Immun. Rev. 120:137-183 (1991)).

The five CD1 genes reveal exon and domain structure (α1, α2, α3) similarity to MHC class I genes. The encoded proteins are however only distantly related in sequence. All CD1 family members share a conserved α3 domain; however, even this domain shows only 32% homology in amino acid sequence with consensus residues of class I MHC α3 domains.

Another major difference between MHC and CD1 molecules is polymorphism. Human MHC genes are extremely polymorphic in that multiple alleles have been described at each known MHC locus. In contrast, CD1 genes do not show the high levels of polymorphism found in MHC class I and II. As an example, individual humans express the same or nearly the same CD1 heavy chain sequences. Despite these differences, the CD1 molecules, like MHC class I molecules, are expressed as large subunits (heavy chains) non-covalently associated with $\beta_2$-microglobulin (Van Agthoven, A., and Terhorst, C., J. Immunol. 128:426-432 (1982); Terhorst, C., et al., Cell 23:771-780 (1981)).

Five CD1 genes have thus far been identified in humans: CD1a, CD1b, CD1c, CD1d and CD1e. Four of the five CD1 gene products, CD1a, CD1b, CD1c and CD1d, have been defined serologically, and are distinguished by unique heavy chains with approximate molecular weights of 49 kDa, 45 kDa, 43 kDa and 48 kDa respectively (Amiot, M., et al., J. Immunol. 136:1752-1758 (1986); Porcelli, S., et al., Immunol. Rev. 120:137-183 (1991); Bleicher, P. A., et al., Science 250:679-682 (1990)). CD1 molecules are displayed on a number of APCs including Langerhans cells (i.e., the major dendritic antigen presenting cells in the skin), activated B-cells, dendritic cells in lymph nodes, and activated blood monocytes (Porcelli, S., et al., Nature 360:593-597 (1992); Leukocyte Typing IV, Knapp, W., ed., Oxford University Press, Oxford, U.K., pp. 251-269, 1989; Tissue Antigens, Kissmeyer-Nielsen, F., ed., Munksgard, Copenhagen, Denmark, pp. 65-72, (1989)). In particular, CD1a genes are highly expressed on human Langerhans cells, and the encoded protein is widely used as a marker to identify these cells. Because CD1a is the only CD1 isoform expressed at high levels of Langerhans cells, this suggests CD1a plays a specialized role in the antigen presenting function of these cells. (Sugita et al., Immunity. 1999;11(6):743-52.) In addition, the autoreactivity of T cells for CD1a proteins suggests that mammalian autoantigens bind to CD1a and that CD1a proteins are involved in autoimmune disorders.

The antigens provided by the invention are presented by CD1 molecules, in particular CD1a molecules, and represent a novel class of lipopeptide CD1-presented antigens. One category of these antigens has the structure of Formula I (as shown in FIG. 1), where R can be an alkyl or alkene chain. These antigens can further be classified according to Formula II or III (as shown in FIG. 1), and in either case where R can be an alkyl or alkene chain.

These naturally occurring compounds are expected to have a "CD1a binding motif". Although not intending to be bound by any particular mechanism or theory, the acyl lysine of the antigen is thought to be the CD1a binding motif. Acyl lysines occur naturally in a wide variety of mammalian, bacterial and viral proteins. The invention therefore embraces CD1a-presented antigens that comprise structurally similar CD1a binding motifs. The invention therefore provides antigens comprising a lysine acylated peptide (i.e., a peptide or amino acid sequence comprising an epsilon lysine acylation). Similarly, peptides that are acylated on cysteine correspond to the general motif of a mono-acylated lipopeptide and are also embraced by the invention.

The antigens having the structure of Formula I (as shown in FIG. 1) are referred to as didehydroxymycobactins (DDMs) and are represented by the salicyl-alpha-methyl serine -lysine[acyl]-hydroxybutyrate-lysines. One specific antigen has a nominal mass of 838 Da when detected as a protonated adduct in positive ion mode mass spectrometry, and is referred to as DDM838. (See FIG. 2.)

The invention provides other alpha-methyl serine containing antigens are also provided that have nominal masses of 840 Da, 810 Da and 812 Da in their protonated forms. These compounds are referred to as DDM840, DDM810 and DDM812, respectively, and their structures are provided in FIG. 2. Other structurally related antigens isolated from the same preparation are referred to herein as DDM826 and DDM824.

The acyl chains appear to bind to the CD1a protein, and appear important to recognition by CD1a-expressing cells such as dendritic cells (e.g., Langerhans cells). The chains may be at least 12, at least 13, at least 14, at least 15, at least 16, at least 17, at least 18, at least 19, or at least 20 carbons long and may be saturated or unsaturated. In some instances, unsaturated alkyl chains at least 17 carbons long are preferred. In some embodiments, the chain may contain more than one double bond.

Figure 3:
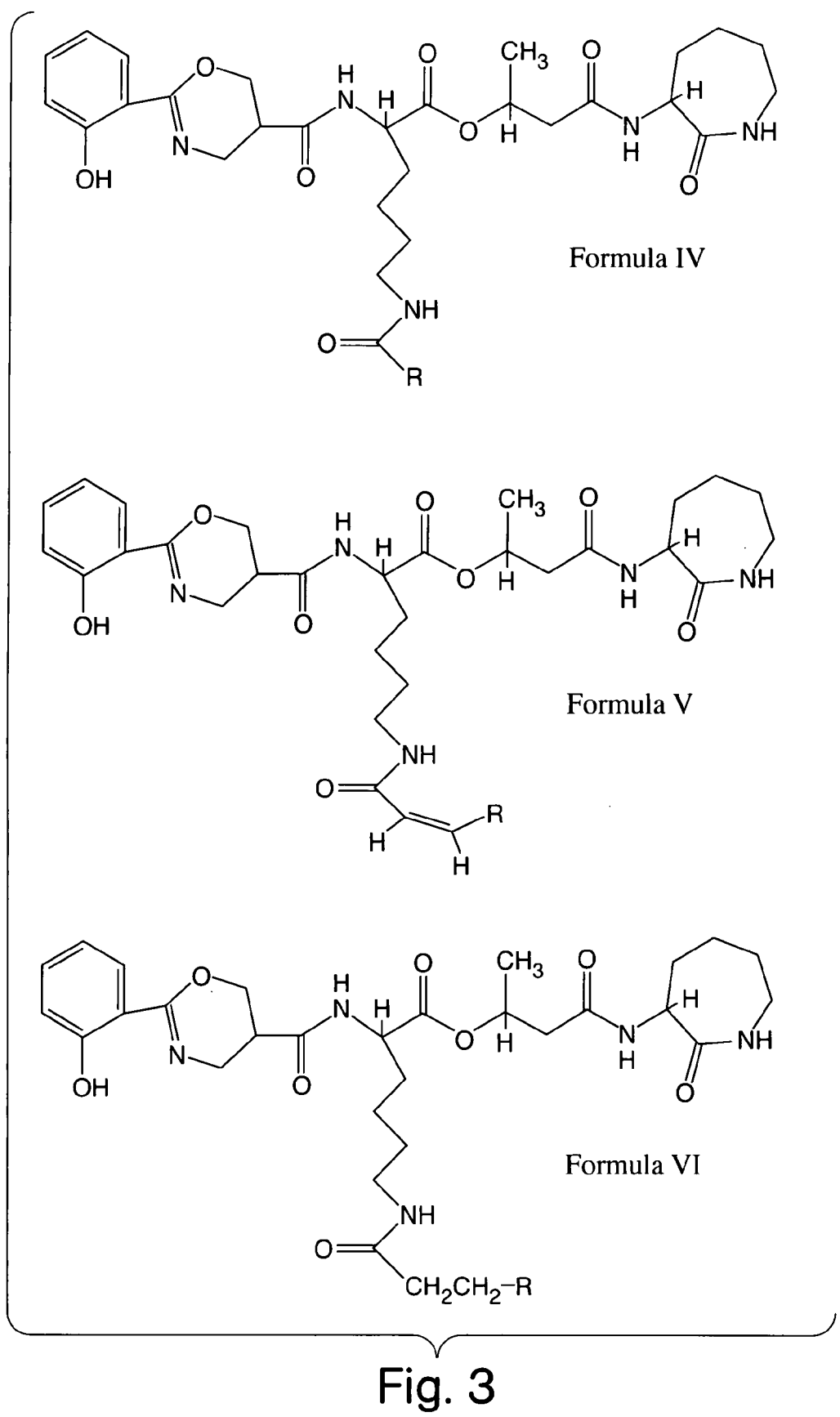
Figure 4:
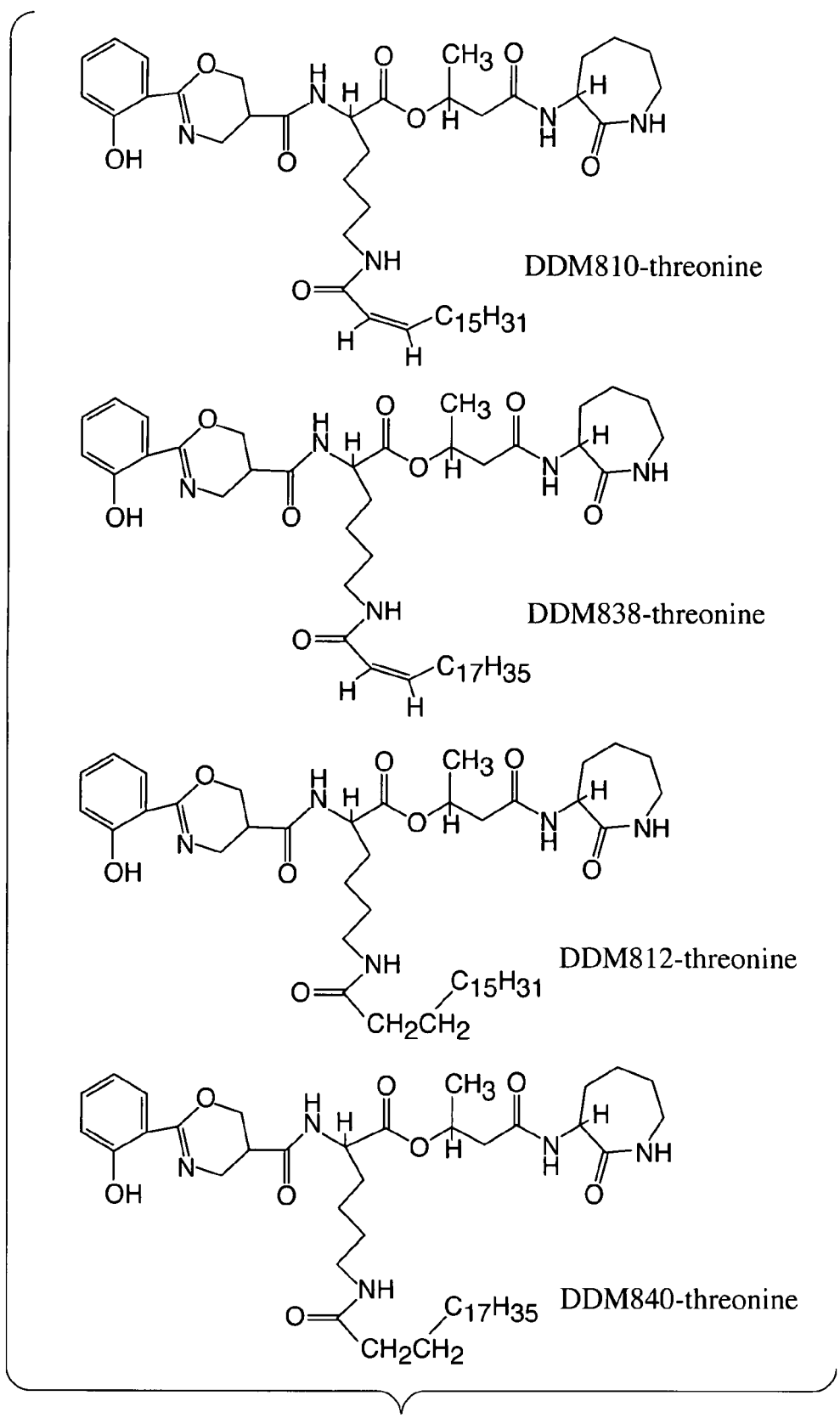

Other natural antigens that are similar to the DDM structure have been isolated and are also embraced by the invention. Some isomers contain serine rather than alpha-methyl serine. Other isomers have a structure of Formula IV which comprise a threonine rather than an alpha-methyl serine, as is shown in FIG. 3. Formula IV antigens can be further categorized as antigens of Formula V and Formula VI, as shown in FIG. 3. Examples of these compounds can be found in FIG. 4, and are referred to as DDM810-threonine, DDM838-threonine, DDM812-threonine, and DDM840-threonine.

Still further isomers include those antigens in which the hydroxyl group on the beta-hydroxy butyrate moiety is in the alpha position. In addition, the beta-hydoxy butyrate moiety can be substituted with a hydroxypentanoic acid moiety.

The crystal structure of CD1a shows that the antigen-binding groove is composed of an F' pocket, which is wide, largely exposed, and broadly contiguous with the predicted TCR contact surface (Zajonc et al. Nature Immunol. 4:808 (2003). The A' pocket is largely hydrophobic, with no obvious polar groups that could hydrogen bond with the peptidic portion of DDM in the way that MHC molecules bind to peptides. Also, the A' pocket is narrow and terminates deep within the CD1a structure, so that it may act as a ruler to select out acyl chains of a particular length. A molecular model shows that the C20:1 fatty acyl moiety could fit well within the A' pocket, positioning the peptide backbone at the broad junction of the A' and F' pockets, so that it would be available for contact with the TCR. Although the orientation of the peptidic moiety cannot be predicted precisely, the only polar residues in the binding groove are located at the A'-F' junction, so it seems plausible that the same residues that are known to bind the sulfogalactosyl moiety of sulfatide also hydrogen bond with the peptidic portion of DDM (D. M. Zajonc, M. A. Elsliger, L. Teyton, I. A. Wilson, Nature Immunol. 4, 808 (2003).

The newly discovered antigens share some structural homology to mycobactin siderophores but lack two hydroxyl groups present in mycobactins, which confer upon mycobactins their ability to bind iron. The absence of these two hydroxyl groups was determined to be important in the recognition of DDMs by CD1a-restricted T cells, as structural homologs with the two hydroxyl groups are not recognized by T cells. The two hydroxyl moieties, which are present in mycobactin but absent in DDM, form two sites, which mediate high-affinity ($\sim 10^{-26}$ M) binding to iron (G. A. Snow, Bacteriol. Rev. 34, 99 (1970). Consistent with the predicted roles of these hydroxyl groups in iron binding, we found that mycobactin was detected in the iron-bound form solely as $[M+Fe-2H]^+$ at m/z 923.5, whereas DDM was detected solely in the unbound form as a proton adduct at m/z 838.6.

Didehydroxmycobactin most likely functions as an intermediate in mycobactin synthesis. During infection, bacteria must obtain iron from host stores to support a variety of reduction-oxidation reactions necessary for normal bacterial metabolism. Bacteria scavenge iron by producing siderophores, which bind iron with high affinity at or near the bacteria-host interface and deliver iron to the bacterium (J. H. Crosa, C. T. Walsh, Microbiol. Mol. Biol. Rev. 66, 223 (2002). Mycobacteria produce mycobactin and related siderophores, whose synthesis is triggered by depression of mycobactin synthase genes during growth in low-iron conditions (O. Dussurget et al., J. Bacteriol. 181, 3402 (1999). This process normally occurs during growth in host cells and is known to be necessary for M. tuberculosis survival within human macrophages (J. De Voss et al., Proc. Natl. Acad. Sci. U.S.A. 97, 1252 (2000). These considerations suggested that DDM might be synthesized as an intermediate in mycobactin production during intracellular infection.

Because CD1a-restricted T cells are able to kill mycobacteria-infected cells (S. Stenger, K. R. Niazi, R. L. Modlin, J. Immunol. 161, 3582 (1998), CD1a presentation of DDM may represent an early warning system for intracellular pathogen recognition, whereby bacterial metabolites, which are necessary for adapting to intracellular growth, result in T cell activation.

Although several of the aspects and embodiments of the invention are described herein in terms of Formula I antigens, it is to be understood that these aspects and embodiments apply equally to Formula II, III, IV, V and VI antigens.

Figure 7:
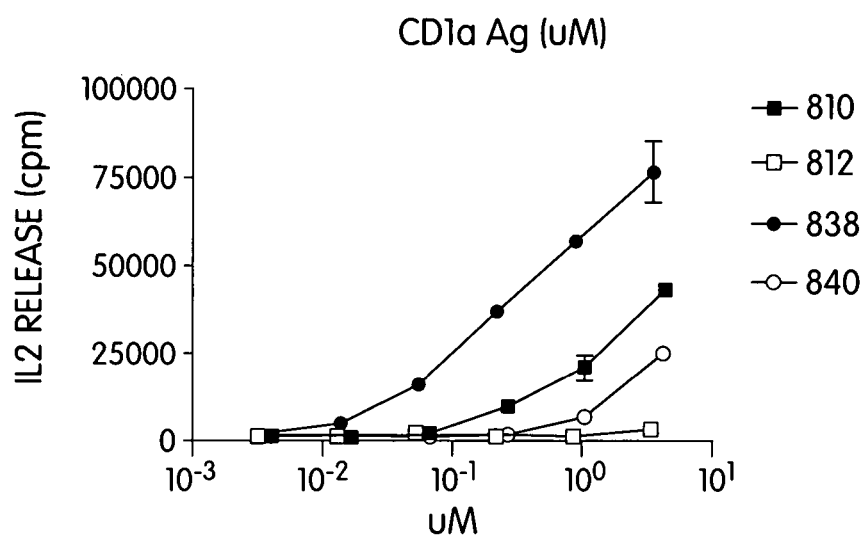
FIG. 7 is a graph showing the response of CD1a-restricted T cell lines to natural homologs of *M. tuberculosis* DDM antigens.

The isolated antigens were tested for their ability to activate T cells. DDM838 gave the most potent T cell response; homologous lipopeptides that had shorter or saturated alkyl or alkene chains were less stimulatory (FIG. 7). In particular, DDM812 and DDM840 showed weaker ability to activate T cells, as compared to DDM838, according to this assay. Natural mycobactins were not recognized, suggesting that the hydroxylation of the lysine residues prevents T cell recognition. Also, lipid fractions containing mycobactic acid, which corresponds to a truncated lipopeptide lacking the butyric acid lysine moiety, were recognized weakly or not at all. Thus, the T cell response was specific for the structure of the peptide and the length and saturation state of the fatty acyl chain. The polypeptide backbone of the antigen appears to serve as the contact for variable regions of the TCR, as in the case for conventional peptide antigens presented by MHC proteins (D. N. Garboczi et al., Nature 384, 134 (1996), K. C. Garcia et al., Science 274, 209 (1996).

T cell recognition of the antigens of the invention requires the presence of a CD1a molecule on the surface of antigen presenting cells. As used herein, a "CD1-presented antigen" refers to an antigen, the recognition of which by T cells requires CD1 protein expression on the surface of an antigen presenting cell (APC). Antigens that are presented by CD1a and thereby recognized by T cells are referred to as "CD1a-presented" antigens. The term "CD1-presented antigen" is used interchangeably with "CD1-restricted antigen". It is to be understood that "CD1-presented antigens" may still be present in a soluble form and not restricted to a form in which they are bound to a CD1 molecule. When the antigen is bound to a CD1 molecule, it can be referred to as a "CD 1-bound antigen". A cell that expresses a CD1 protein is referred to as a "CD1+ cell" or a "CD1-expressing cell". A CD1a-expressing cell may be a cell that naturally expresses CD1a, a cell that is induced to express CD1a for example by culture in GM-CSF and/or IL-4, or it may be a transfectant (i.e., a cell into which an exogenous nucleic acid is introduced and from which the CD1a is expressed). Various CD1a gene sequences are publicly available through GenBank (e.g., Accession Number AAH31645). A "CD1-restricted T cell" is a mature peripheral blood lymphocyte that expresses T cell antigen receptor (TCR) and may be referred to as a TCR+ cell. T cells that bind the antigens of the invention include CD8+ T cells.

The CD1a proteins and/or the CD1a-presented antigens of the invention are displayed on antigen presenting cells. As used herein, "displayed" refers to the process of localizing a protein, such as a CD1 protein, or a complex such as CD1 protein:antigen complex, to the outermost surface of a cell where the protein or complex is accessible to a second cell or to molecules displayed by a second cell. In some instances, antigens are processed with cellular factors in order to be made competent for displaying by an APC. An "antigen presenting cell" refers to a cell that presents antigen to T cells by way of MHC class I or class II molecules or CD1 molecules. One skilled in the art can use procedures known in the art for determining whether a cell is expressing one or more members of the CD1 family of proteins (see U.S. Pat. Nos. 5,679,347; 5,853,737 and 6,238,676 and Porcelli, S., Immun. Rev. 120:137-183 (1991)).

The antigens may be naturally occurring or synthetic. Synthetic antigens may include those derived from nature, which have been subsequently manipulated or modified. Alternatively, they include antigens that have no naturally occurring counterparts. For example, the synthetic antigen may contain the CD1a lipid binding motif of the Formula I compounds attached (e.g., covalently) to a peptide moiety that may be recognized by a T cell.

The invention, in part, provides several CD1a antigens identified and isolated from mycobacteria (e.g., *Mycobacterium tuberculosis*). Mycobacteria are a genus of aerobic intracellular bacterial organisms which upon invasion of their host, survive within endosomal compartments of monocytes and macrophages. Human mycobacterial diseases include tuberculosis (caused by *M. tuberculosis*), leprosy (caused by *M. leprae*), Bairnsdale ulcers (caused by *M. ulcerans*), and various other infections caused by *M. marinum, M. kansasii, M. scrofulaceum, M. szulgai, M. xenopi, M. fortuitum, M. chelonei, M. haemophilum* and *M. intracellulare* (Wolinsky, E., Chapter 37 in Microbiology: Including Immunology and Molecular Genetics, 3rd Ed., Harper & Row, Philadelphia, 1980; Daniel, T. M., Miller, R. A. and Freedman, S. D., Chapters 119, 120 and 121, respectively, in Harrison's Principles of Internal Medicine, 11th Ed., Braunwald, E., et al., eds., McGraw-Hill, New York, 1987).

The mycobacteria from which the antigen is isolated can be grown in conditions that stimulate production of the antigen. For example, the mycobacteria can be grown in iron free media. Iron free media are known to those of skill in the art. As another approach, the mycobacteria may be naturally incapable of DDM hydroxylation, or may be genetically manipulated to be so. For example, the mycobacteria may be incapable of DDM hydroxylation due to a mutation in the MbtG gene. Alternatively, the mycobacteria may be genetically engineered to overproduce mycobactin-like compounds. These genetically engineered mycobacteria may comprise null mutations at the IdeR locus or at loci that encode iron-binding repressors of mycobactin synthesis. Null mutations are mutations that result in low or no gene product production from the indicated locus. A null mutation can take various forms as is known in the art. Iron regulation and targets suitable for mutation in mycobacteria are further described by Rodriguez et al., (Mol. Microbiol. 2003. 47(6): 1485-1494.)

The antigens were discovered by isolating a fraction with T cell stimulating activity from a *M. tuberculosis* lysate. The lysates were tested for their ability to stimulate the CD1a T cell line CD8-2 (Rosat et al., J. Immunol. 1999 162:366-371). The isolation process involved extraction of whole *M. tuberculosis* with chloroform/methanol (2:1) to obtain total mycobacterial lipids (Moody et al., Science 1997 278(5336): 283-6). The antigen was isolated using cold acetone precipitation which allowed the antigen to be recovered in the liquid organic phase, while contaminating phospholipids were precipitated and thereby removed from the mixture. These methods resulted in approximately a three fold enrichment of the antigen and reduction of contaminants. The organic phase was resuspended in chloroform and loaded onto columns with a silica matrix. The column was eluted with organic solvents of increasing polarity (chloroform, acetone, methanol) to separate the lipids into broad classes. The antigenic activity was recovered in methanol-eluting fractions that were then subjected to higher resolution chromatographic methods to further purify the polar lipid fraction. These methods included lipid preparative silica thin layer chromatography, silica extraction cartridges eluted with complex systems of organic and aqueous solvents, and DEAE column chromatography. This resulted in approximately another 10-fold enrichment.

The antigens were enriched another 5-fold or more (and in some instances, purified to homogeneity) with a reversed phase HPLC method performed on C8 matrices and eluted with a gradient of solvent mixtures. Reversed phase separations were accomplished using a Vydac C-18 column (25 cm, 4.6 mm internal diameter). A binary gradient was set up using 5:3:2 (v:v:v) methanol:acetonitrile:water as the A phase and 93:7 isopropanol:hexane as the B phase. The flow rate was 0.7 mL/min throughout the chromatographic run. The gradient started at 20% B and was increased to 60% B over 35 min to elute DDMs. This allowed DDMs with varying acyl chain length and degree of unsaturation to be separated. Dual channel UV detection was used at 214 nm and 305 nm to provide both general and DDM selective detection.

Mass spectrometry of stimulatory compounds from two-dimensional TLC sub-fractions showed ions MH+ with mass to charge ratio 838, 840, 824, 826, 812 and 810. Detailed tandem mass spectral experiments (i.e., collision induced dissociation mass spectrometry) were performed on DDM838 which adducted a single proton to give an ion m/z 838. Identification of fragments at m/z 624 and m/z 642 suggested that the antigen at m/z 838 had a primary cleavage site leading to products that are similar but not identical to mycobacterial mycobactins. Further analysis indicated that the 838 antigen is similar to mycobactin except that DDM838 had amide groups substituting the two hydroxyamides found in mycobactin. Absence of these two hydroxyl groups was important for the antigenic function of DDMs since purified mycobactins, which have hydroxyl lysines, did not stimulate a CD1a-restricted T cell response.

Mass spectral analysis of high performance liquid chromatography (HPLC) fractions provided further evidence that ions at m/z 838 and m/z 840 contained CD1a stimulating activity. Using HPLC with ultraviolet absorbance and positive ion mode mass spectroscopy, antigens that were detected at m/z 838, m/z 840, m/z 824, m/z 826, m/z 810 and m/z 812 were purified to homogeneity. A comparison of mass spectra of the antigen fraction with standards known to contain serine or threonine indicated that some antigens contained alpha-methyl serine. This was confirmed by gas chromatography-mass spectrometric analysis of derivatized amino acids. In addition to the above isolation methods, the antigens provided can be synthesized de novo. Mycobactins have been successfully synthesized as described in Vergne et al., Nat. Prod. Rep. 2000 17(1):99-116. The antigens of the invention can similarly be synthesized using a precursor compound that lacks hydroxyamides.

In various aspects of the invention, the antigens are provided in an isolated form. The term "isolated" as used herein refers an antigen that is substantially free of proteins, lipids, carbohydrates or other materials with which it is naturally associated. One skilled in the art can purify lipopeptides, using standard techniques purification such as those described herein.

The ultimate antigen preparation is at least 90% pure, more preferably 95% pure, and even more preferably 99% pure for a specific antigen. As used herein, a composition containing an "isolated" antigen refers to a composition that is at least 95% pure, and more preferably 96%, 97%, or 98% pure, and even more preferably 99% pure, 99.5% pure or 99.9% pure.

In other aspects of the invention, compositions, and preferably pharmaceutical compositions (as defined herein), are provided that comprise a substantially pure composition of one or more antigens of the invention. As used herein, a substantially pure composition is a composition that contains at least 50% of the antigen. In some embodiments, the substantially pure composition may contain at least 55%, at least 60%, at least 65%, at least 70%, at least 75%, at least 80%, at least 85%, or at least 90% of the antigen (and every integer therebetween as if explicitly recited herein). These compositions may have various embodiments, including those recited herein for compositions of isolated antigen.

As used herein, a "sample" is any solution, emulsion, suspension, or extract, which can be tested for the presence of a CD1a antigen. A sample may be, but is not limited to, a soluble extract or an organic extract. As described above, a sample can be first fractionated (i.e., subjected to conditions or procedures that separate its components based on physical or chemical properties such as, but not limited to, size, charge, solubility, or composition) using conventional procedures. Examples of procedures include, but are not limited to, selective precipitation, organic extraction, normal or reversed phase high performance chromatography, and ion exchange chromatography. These methods are known to those of ordinary skill in the art. The fractions of the sample are then tested for the presence of the antigen. Some aspects of the invention employ bodily samples such as those harvested from a subject. These are discussed herein.

Antigens may also be isolated by screening test compounds for their ability to bind to CD1a particularly as compared to the CD1a -presented antigens of the invention. In these and other assays, the CD1a may be isolated (i.e., cell free) or it may be cell bound. In one example, a sample containing a putative antigen is contacted with a purified CD1a. If the CD1a is cell bound, and if the cell is activatable upon binding of CD1a by an antigen, then the antigen can be isolated based on its ability to bind to and activate the cell or a CD1a-restricted T cell line. As used herein, "contacting" is the process of combining one or more entities. If the CD1a is isolated the resulting antigen:CD1a complex is then separated from the sample and further analyzed (e.g., by dissociating the antigen from the CD1a).

The invention provides a method for identifying a CD1a-restricted antigen using a competition binding assay. The competition binding assay measures the ability of a test compound to compete away binding of a CD1a-presented antigen of the invention to CD1a. In some instances, the test compound can be screened either before or after the competition binding assay for the ability to bind to CD1a. As an example, a CD1a protein is contacted with an isolated CD1a-restricted antigen (such as those provided by the invention) in the presence and absence of the test compound. The test compound may be naturally or non-naturally occurring. It may be isolated from natural sources or synthesized de novo. According to one form of the assay, a control level of binding between the CD1a protein and the isolated CD1a-restricted antigen (i.e., the known antigen is determined in the absence of the test compound, and a test level of binding between the CD1a protein and the isolated CD1a-restricted antigen is determined in the presence of the test compound. A test level of binding that is less than a control level of binding indicates that the test compound is a CD1a-restricted antigen. The isolated CD1a-restricted antigen used in these assays may have a structure of Formula I, Formula II, Formula III, Formula IV, Formula V or Formula VI, where R is an alkyl chain or an alkene chain. More specifically, the antigen may be DDM838, DDM840, DDM812 or DDM810, or it may be DDM838-threonine, DDM840-threonine, DDM812-threonine or DDM810-threonine. As stated above, the CD1a protein may be isolated (e.g., cell free), and in this form it may be soluble or attached to a solid substrate (e.g., cell free). Alternatively, the CD1a protein may be cell-bound (i.e., present in the form of a CD1a -expressing cell). The CD1a -expressing cell may be a human dendritic cell such as a Langerhans cell.

Figure 6:
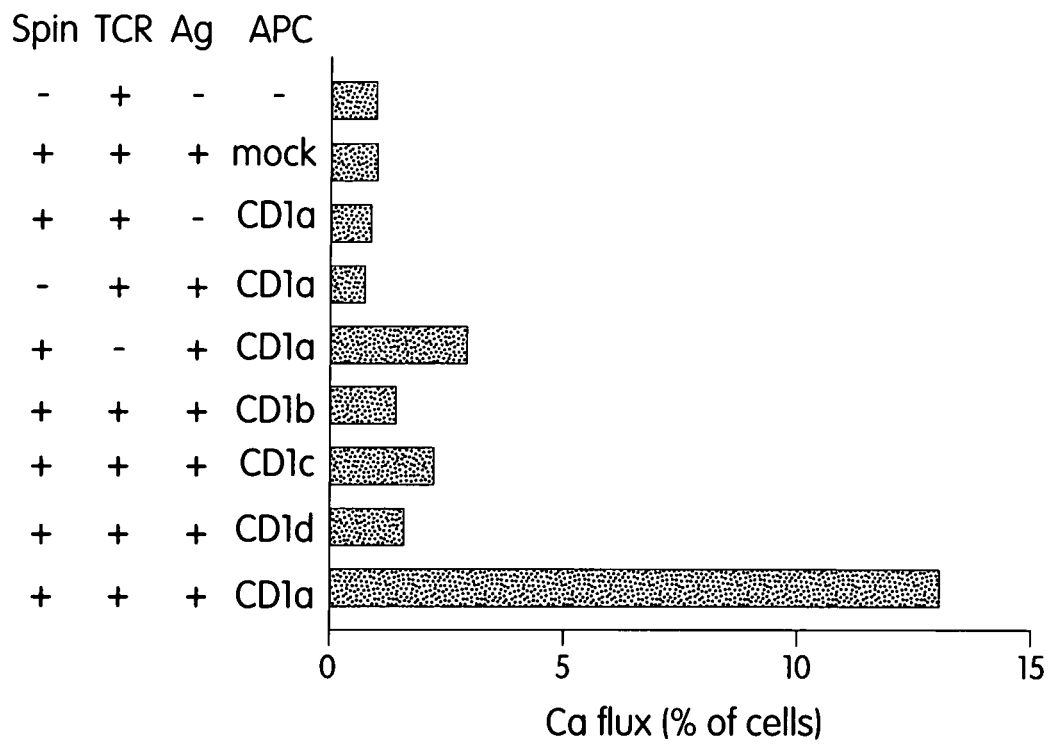

The antigen or antigen:CD1a complexes can be further screened for their ability to activate CD1a-restricted T cells using T cell stimulation assays as described herein. The antigens provided herein were identified with T cell activation assays to determine the relative ability of purified fractions to activate T cells. These assays were carried out essentially as described in U.S. Pat. Nos. 5,679,347; 5,853,737; and 6,238,676, and in Rosat et al., J. Immunol. 1999, 162:366-371, except that a range of antigen presenting cells were used that expressed different CD 1 molecules. The ability of the 838 Da antigen to activate CD1a-restricted T cells is shown in FIGS. 6 and 7. A "CD1-restricted T cell" is a mature peripheral blood lymphocyte that expresses T cell antigen receptors, or is TCR$^+$. The T cells used to identify the antigens of the invention are CD8+.

Methods of culturing T cells in vitro, and of immortalizing T cells via fusion to non-growth restricted cells such as myelomas, have been described. Paul, W. E., et al., Nature 294:697-699 (1981); Williams, N., Nature 296:605-606 (1982). T cell populations can be enriched to obtain isolated T cell clones which are reactive to CD1a-presented antigens. A population of T cells is allowed to divide and a subpopulation of mixed T cells is isolated based on proliferation in the presence of CD1a$^+$ APCs and CD1a-presented antigen, or on cytolytic activity against transfected cells expressing CD1a molecules in the presence of a CD1a-presented antigens.

The CD1 antigens can also be used to modulate an immune response. To "modulate an immune response" as used herein means to enhance or inhibit a pre-existing immune response, to stimulate a non-existent immune response, and/or to alter the characteristics of an immune response. Inhibiting an immune response means that the immune response is lessened from a pre-treatment level, and may include but is not limited to a complete abrogation of an immune response. As used herein, the term "inhibit" means a reduction in symptoms associated with a condition, or complete elimination of the condition, as determined by a medical practitioner. When the antigens are used to enhance the immunity of a subject, it is intended that the antigens can enhance a pre-existing immune response and/or stimulate a non-existent immune response. If a subject has an infection such as a bacterial infection, then the antigen provided herein may be used to stimulate an immune response and/or enhance a pre-existing immune response. If a subject is undergoing an inappropriate immune response that is associated with the antigen, then administration of the antigen or an antigen antagonist, as described herein, may be used to inhibit or alter the characteristics of the immune response. Altering the characteristics of an immune response can include switching an immune response from a Th2 immune response to a Th1 immune response, or vice versa. For optimal protection against infection by most bacterial pathogens including mycobacteria, the immune response is polarized towards a Th1 immune response. Preferably, the antigens are DDM838 or DDM810, less preferably DDM840.

These antigens provided herein can be used as antigens, and also as adjuvants and immunomodulators. Generally, these antigens act at least, in part, by inducing a CD1 immune response, and in particular a CD1a immune response. A "CD1 immune response", as used herein, is an immune response that involves antigen presentation by an antigen presenting cell that expresses a CD1 molecule on its surface to a T cell that recognizes the presented antigen via its TCR in the context of CD1. T cells that recognize antigen presented in the context of CD1 become activated as a result, and may respond in a number of ways. For example, these T cells can lyse target cells (e.g., cells infected with mycobacteria such as *M. tuberculosis, M. leprae, M. ulcerans, M. marinum, M. kansasii, M. scrofulaceum, M. szulgai, M. xenopi, M. fortuitum, M. chelonei, M. haemophilum, M. intracellular*, etc.). T cells may also respond by secreting γ-interferon which in turn can polarize an immune response towards a Th1 response. The antigens therefore are useful in generating effector T cells during microbial infection.

The antigen can also be used to modulate autoimmune responses. Previous work has shown that some CD1 molecules are recognized by $CD4^-CD8^-$ (DN) T cell lines derived from patients with SLE. Porcelli, et al., Nature 341:447-450 (1989). Leukemic cells expressing CD1 molecules were lysed by T cells independent of MHC restriction, even though no foreign (non-self) antigen was present. (Shamshiev et al. Eur J Immunol. 1999, 29(5):1667-75; Gumperz et al. Immunity. 2000 February;12(2):211-21.) Human cells produce protein sequences that are acylated on lysine or other amino acid residues to produce lipopeptides with structural homology to the lipopeptide antigens described herein. Accordingly, the methods described herein can be used in the treatment of autoimmune diseases involving such structurally similar proteins. As an example, the human interleukin 1 alpha chain has a sequence that is acylated and it thereby resembles the DDM motif.

The antigens of the invention can be used as adjuvants given their ability to modulate an immune response. Accordingly, they may be administered together with another antigen (e.g., a CD1 restricted antigen or an MHC restricted antigen) or they may be administered to a subject that is at risk of being exposed to an antigen passively or actively. Subjects that may be passively exposed to an antigen can be one that is in an environment or profession in which exposure to an antigen likely. Examples include being in a country in which particular infectious agents are pandemic, or working in an environment in which infectious agents are common (e.g., a doctor's office or hospital), or being subject to or at risk of a bioterrorist attack using microbial pathogens (such as anthrax or small pox). Active exposure means deliberate exposure to an antigen, such as occurs with a vaccination. Accordingly, the antigens may be used in conjunction with vaccine compositions in order to enhance an immune response to the antigen provided in the vaccine.

The antigens of the invention can be administered together with an adjuvant. In these aspects of the invention, an adjuvant is any molecule or compound (except for the CD1a antigens described herein) which can stimulate a humoral and/or cellular immune response. Adjuvants include, for instance, adjuvants that create a depo effect, immune stimulating adjuvants, adjuvants that create a depo effect and stimulate the immune system, and mucosal adjuvants. In some embodiments, the adjuvants is preferably an immune stimulating adjuvant.

An "adjuvant that creates a depo effect" as used herein is an adjuvant that causes an antigen to be slowly released in the body, thus prolonging the exposure of immune cells to the antigen. Examples include but are not limited to alum (e.g., aluminum hydroxide, aluminum phosphate); or emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720, AirLiquide, Paris, France); MF-59 (a squalene-in-water emulsion stabilized with Span 85 and Tween 80; Chiron Corporation, Emeryville, Calif.; and PROVAX (an oil-in-water emulsion containing a stabilizing detergent and a micelle-forming agent; IDEC, Pharmaceuticals Corporation, San Diego, Calif.).

An "immune stimulating adjuvant" is an adjuvant that causes activation of a cell of the immune system. It may, for instance, cause an immune cell to produce and secrete cytokines. Examples include but are not limited to saponins purified from the bark of the *Q. saponaria* tree, such as QS21 (a glycolipid that elutes in the $21^{st}$ peak with HPLC fractionation; Antigenics Inc. Woburn, Mass.); poly[di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonylmuramyl dipeptide (t-MDP; Ribi); OM-174 (a glucosamine disaccharide related to lipid A; OM Pharma S A, Meyrin, Switzerland); and Leishmania elongation factor (a purified *Leishmania* protein; Corixa Corporation, Seattle, Wash.).

An "adjuvant that creates a depo effect and stimulates the immune system" is a compound that has both of the above-identified functions. Examples include but are not limited to ISCOMS (immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

A "mucosal adjuvant" as used herein is an adjuvant that is capable of inducing a mucosal immune response in a subject when administered to a mucosal surface in conjunction with an antigen. Examples include but are not limited to bacterial toxins: e.g., Cholera toxin (CT), CT derivatives including but not limited to CT B subunit (CTB) (Wu et al., 1998, Tochikubo et al., 1998); CTD53 (Val to Asp) (Fontana et al., 1995); CTK97 (Val to Lys) (Fontana et al., 1995); CTK104 (Tyr to Lys) (Fontana et al., 1995); CTD53/K63 (Val to Asp, Ser to Lys) (Fontana et al., 1995); CTH54 (Arg to His) (Fontana et al., 1995); CTN107 (His to Asn) (Fontana et al., 1995); CTE114 (Ser to Glu) (Fontana et al., 1995); CTE112K (Glu to Lys) (Yamamoto et al., 1997a);

CTS61F (Ser to Phe) (Yamamoto et al., 1997a, 1997b); CTS106 (Pro to Lys) (Douce et al., 1997, Fontana et al., 1995); and CTK63 (Ser to Lys) (Douce et al., 1997, Fontana et al., 1995), Zonula occludens toxin, zot, *Escherichia coli* heat-labile enterotoxin, Labile Toxin (LT), LT derivatives including but not limited to LT B subunit (LTB) (Verweij et al., 1998); LT7K (Arg to Lys) (Komase et al., 1998, Douce et al., 1995); LT61F (Ser to Phe) (Komase et al., 1998); LT112K (Glu to Lys) (Komase et al., 1998); LT118E (Gly to Glu) (Komase et al., 1998); LT146E (Arg to Glu) (Komase et al., 1998); LT 192G (Arg to Gly) (Komase et al., 1998); LTK63 (Ser to Lys) (Marchetti et al., 1998, Douce et al., 1997, 1998, Di Tommaso et al., 1996); and LTR72 (Ala to Arg) (Giuliani et al., 1998), Pertussis toxin, PT. (Lycke et al., 1992, Spangler B D, 1992, Freytag and Clemments, 1999, Roberts et al., 1995, Wilson et al., 1995) including PT-9K/129G (Roberts et al., 1995, Cropley et al., 1995); Toxin derivatives (see below) (Holmgren et al., 1993, Verweij et al., 1998, Rappuoli et al., 1995, Freytag and Clements, 1999); Lipid A derivatives (e.g., monophosphoryl lipid A, MPL) (Sasaki et al., 1998, Vancott et al., 1998; Muramyl Dipeptide (MDP) derivatives (Fukushima et al., 1996, Ogawa et al., 1989, Michalek et al., 1983, Morisaki et al., 1983); Bacterial outer membrane proteins (e.g., outer surface protein A (OspA) lipoprotein of *Borrelia burgdorferi*, outer membrane protine of *Neisseria meningitidis*) (Marinaro et al., 1999, Van de Verg et al., 1996); Oil-in-water emulsions (e.g., MF59) (Barchfield et al., 1999, Verschoor et al., 1999, O'Hagan, 1998); Aluminum salts (Isaka et al., 1998, 1999); and Saponins (e.g., QS21) Aquila Biopharmaceuticals, Inc., Worcester, Mass.) (Sasaki et al., 1998, MacNeal et al., 1998), ISCOMS, MF-59 (a squalene-in-water emulsion stabilized with Span 85 and Tween 80; Chiron Corporation, Emeryville, Calif.); the Seppic ISA series of Montanide adjuvants (e.g., Montanide ISA 720; AirLiquide, Paris, France); PROVAX (an oil-in-water emulsion containing a stabilizing detergent and a micell-forming agent; IDEC Pharmaceuticals Corporation, San Diego, Calif.); Syntext Adjuvant Formulation (SAF; Syntex Chemicals, Inc., Boulder, Colo.); poly[di(carboxylatophenoxy) phosphazene (PCPP polymer; Virus Research Institute, USA) and Leishmania elongation factor (Corixa Corporation, Seattle, Wash.).

The vaccines can be formulated using a purified antigen or using a CD1a-bound antigen. Because CD1a -presented antigens are presented to T cells as a complex of antigen and CD1a, the use of an antigen:CD1a complex or an antigen:CD1a$^+$ cell complex can, in some cases, provide superior immunization properties. A skilled artisan can employ routine formulation procedures in order to formulate an isolated CD1a-presented antigen for use as a vaccine. See Remington's Pharmaceutical Sciences, 18th Ed., Gennaro, A. R., ed., Mack, Easton, (1990); The Pharmacologist Basis of Therapeutics, 7th Ed., Gilman, A. G., et al., eds., MacMillan, New York, (1985).

The antigens of the invention can also be administered to a subject together with a cytokine. Examples of cytokines include, but are not limited to IL-1, IL-2, IL-4, IL-5, IL-6, IL-7, IL-10, IL-12, IL-15, IL-18 granulocyte-macrophage colony stimulating factor (GM-CSF), granulocyte colony stimulating factor (GCSF), interferon-γ (γ-IFN), IFN-a, tumor necrosis factor (TNF), TGF-β, FLT-3 ligand, and CD40 ligand. Cytokines play a role in directing the T cell response. Helper (CD4+) T cells orchestrate the immune response of mammals through production of soluble factors that act on other immune system cells, including other T cells. Most mature CD4+ T helper cells express either a Th1 or a Th2 cytokine profile. In some embodiments it is preferred that the cytokine be a Th1 cytokine.

The antigens of the invention can also be used in combination with dendritic cell based vaccines. For example, the antigen can be loaded onto dendritic cells (e.g., autologous dendritic cells) that have been treated to induce CD1a expression, and these cells can then be introduced into a subject. Most if not all dendritic cells normally express CD1a, especially if treated with GM-CSF and IL-4 or mycobacterial lipids.

CD1$^+$ cells (e.g., CD1a+ human dendritic cells) used in the various aspects of the invention can naturally express the CD1 molecule or can be manipulated to do so. For instance, cells can be transfected with an expression vector encoding the CD1 molecule of interest. As used herein, "genetically engineered" refers to any human manipulation intended to introduce genetic change. In this instance, cells can be genetically engineered to express a CD1 molecule. In addition, a cell can also be induced to express CD1 by contacting the cell with one or more cytokines such as GM-CSF and IL-4 or mycobacterial lipid preparations. One skilled in the art can readily vary the contacting time, cytokine type and concentration, and contacting conditions to induce CD1, or in particular, CD1a expression. As used herein, "expressing" refers to the process of producing a gene product by transcription of a DNA molecule to generate a corresponding mRNA molecule that is translated into a polypeptide.

The invention provides methods for modulating immune responses in subjects in need thereof. A "subject" shall mean a human or vertebrate animal including but not limited to a dog, cat, horse, cow, pig, sheep, goat, chicken, non-human primate (e.g., monkey), fish (aquaculture species, e.g., salmon), rabbit, rat, and mouse. A subject in need of immunomodulation may be a subject having or at risk of developing a condition that can be therapeutically benefited by an immune response. Examples of conditions include infections such as mycobacterial, bacterial, viral, fungal, and parasitic infections, autoimmune diseases, cancers, allergies, asthma, and the like. A subject having one of these conditions can be readily identified by a medical practitioner as these conditions are known and the symptoms associated with each are also known. A subject at risk of developing one of these conditions is similarly readily identified. Examples include subjects that have been exposed or are likely to be exposed to an infectious organism such as a bacterium, virus, fungus, or parasite. Further examples include subjects that have been exposed or are likely to be exposed to a carcinogen, in the case of cancer. Carcinogens are agents with suspected cancer causing activity.

The antigens can therefore be used to treat subjects having or at risk of developing a condition that could benefit from an immune response. As used herein, the term "treat" includes prevention of a condition by administering the antigen prophylactically. Vaccine-induced acquired protective immunity, as used herein, refers to an immunity which occurs as a result of deliberate exposure to an antigen (the compounds of the invention) in a form and dose sufficient to stimulate an immune response to the antigen and, thereby, render the subject immune to subsequent challenge with the antigen. The invention, therefore, provides methods and compositions for enhancing vaccine-induced immunity by administering a vaccine comprising an antigen of the invention. Methods for enhancing vaccine-induced protective immunity are useful for the treatment or prevention of a variety of diseases including but not limited to infectious disease (i.e., infections).

A "subject in need of treatment" embraces inter alia a subject having an autoimmune disease, as well as a subject at risk of developing an autoimmune disease.

A subject having an infection or an autoimmune disease is a subject with at least one identifiable sign, symptom, or laboratory finding sufficient to make a diagnosis of an infectious disorder or of an autoimmune disease in accordance with clinical standards known in the art for identifying such disorders. Examples of such clinical standards can be found in *Harrison's Principles of Internal Medicine*, 14th Ed., Fauci A S et al., eds., McGraw-Hill, New York, 1998. In some instances, a diagnosis of an infection will include identification of an infectious organism or agent by culture of the infectious organism or agent from a body fluid or tissue obtained from the subject. Examples of infectious organisms and infectious agents, including but not limited to bacteria, viruses, protozoa, and fungi, are given below.

Examples of mycobacteria include those listed herein as well as *M. avium intracellulare*, *M. malmoense*, and *M. xenopi*. In some embodiments, subjects have both a viral infection (such as HIV infection) and a mycobacterial infection (such as a *M. avium intracellulare*, *M. malmoense*, and *M. xenopi* infections).

Examples of infectious bacteria include but are not limited to: *Acinetobacter* spp., *Actinomyces israelli*, *Bacillus anthracis*, *Bacteroides* spp., *Bordetella pertussis*, *Borrelia burgdorferi*, *Brucella melitensis*, pathogenic *Campylobacter* spp., *Clostridium difficile*, *Clostridium perfringens*, *Clostridium tetani*, *Corynebacterium diphtheriae*, other *Corynebacterium* spp., *Enterobacter aerogenes*, *Enterococcus* spp., *Erysipelothrix rhusiopathiae*, *Escherichia coli*, *Francisella tularensis*, *Fusobacterium nucleatum*, *Haemophilus influenzae*, *Helicobacter pylori*, *Klebsiella pneumoniae*, *Legionella pneumophilia*, *Leptospira* spp., *Listeria monocytogenes*, *Mycobacteria* spp. (e.g., *M. tuberculosis*, *M. avium*, *M. gordonae*, *M. intracellulare*, and *M. kansasii*), *Neisseria gonorrhoeae*, *Neisseria meningitidis*, *Nocardia asteroides*, *Nocardia brasiliensis*, *Pasturella multocida*, *Peptostreptococcus* spp., *Proteus* spp., *Pseudomonas aeruginosa*, other *Pseudomonas* spp., *Rickettsia*, *Salmonella* spp., *Serratia* spp., *Shigella* spp., *Staphylococcus aureus*, *Streptobacillus moniliformis*, *Streptococcus* (anaerobic spp.), *Streptococcus* (viridans group), *Streptococcus agalactiae* (Group B Streptococcus), *Streptococcus bovis*, *Streptococcus faecalis*, *Streptococcus pneumoniae*, *Streptococcus pyogenes* (Group A Streptococcus), *Treponema pallidum*, *Treponema pertenue*, *Vibrio cholerae*, other *Vibrio* spp., and *Yersinia* spp.

Examples of infectious viruses include but are not limited to: *Adenoviridae* (most adenoviruses); *Arena viridae* (hemorrhagic fever viruses); *Birnaviridae*; *Hepadnaviridae* (Hepatitis B virus); *Bungaviridae* (e.g., Hantaan viruses, bunga viruses, phleboviruses and Nairo viruses); *Calciviridae* (e.g., strains that cause gastroenteritis); *Coronaviridae* (e.g., coronaviruses);*Filoviridae* (e.g., ebola viruses); *Flaviridae* (e.g., dengue viruses, encephalitis viruses, yellow fever viruses); *Herpesviridae* (herpes simplex virus (HSV) 1 and 2, varicella zoster virus, cytomegalovirus (CMV), herpes virus; *Iridoviridae* (e.g., African swine fever virus); *Orthomyxoviridae* (e.g., influenza viruses); *Paramyxoviridae* (e.g., parainfluenza viruses, mumps virus, measles virus, respiratory syncytial virus); *Parvovirida* (parvoviruses); *Papovaviridae* (papilloma viruses, polyoma viruses); *Picornaviridae* (e.g., polio viruses, hepatitis A virus; enteroviruses, human Coxsackie viruses, rhinoviruses, echoviruses); *Poxviridae* (variola viruses, vaccinia viruses, pox viruses); *Reoviridae* (e.g., reoviruses, orbiviurses and rotaviruses); *Retroviridae* (e.g., human immunodeficiency viruses, such as HIV-1 (also referred to as HTLV-III, LAV or HTLV-III/LAV, or HIV-III, and other isolates, such as HIV-LP; *Rhabdoviridae* (e.g., vesicular stomatitis viruses, rabies viruses); *Togaviridae* (e.g., equine encephalitis viruses, rubella viruses); and unclassified viruses (e.g., the etiological agents of spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious fungi include but are not limited to: *Aspergillus* spp., *Blastomyces dermatitidis*, *Candida albicans*, other *Candida* spp., *Coccidioides immitis*, *Cryptococcus neoformans*, *Histoplasma capsulatum*, and *Rhizopus* spp.

Other infectious organisms include but are not limited to: *Plasmodium* spp. (e.g., *Plasmodium falciparum*, *Plasmodium knowlesi*, *Plasmodium malariae*, *Plasmodium ovale*, and *Plasmodium vivax*), *Babesia divergens*, *Babesia microti*, *Chlamydia trachomatis*, *Giardia* spp., *Leishmania braziliensis*, *Leishmania donovani*, *Leishmania major*, *Leishmania tropica*, *Toxoplasma gondii*, *Trichinella spiralis*, and *Trypanosoma cruzi*, as well as the mycobacterial species referred to herein.

A subject at risk of developing an infection is a subject with an identifiable risk factor for developing an infection. For example, a subject at risk of developing an infection can include an individual with a known or suspected exposure to another individual with an infection (e.g., medical or military personnel). Alternatively, a subject at risk of developing an infection can include an individual with a known or suspected exposure to an agent or vector associated with an infection. Yet other examples of a subject at risk of developing an infection include a subject that is immunocompromised, a subject about to undergo surgery, and a subject that has recently undergone surgery.

A subject that is immunocompromised is a subject with reduced capacity to mount an effective immune response to an infectious agent. Such subjects may have, for example, an immune system that is immature or that is suppressed in association with exposure to certain pharmacological agents, suppressed in association with exposure to irradiation, suppressed in association with a chromosomal defect, suppressed in association with a hereditary or inborn metabolic defect or enzyme deficiency, suppressed in association with an antibody deficiency, suppressed in association with a defect in the ability of T cells to process and/or present antigen, suppressed in association with a nutritional deficiency, suppressed in association with an infection that directly affects cells of the immune system (e.g., HIV), suppressed in association with a neoplasm. These and other examples of conditions that cause a subject to be immunocompromised can be found in *Harrison's Principles of Internal Medicine*, 14th Ed., Fauci A S et al., eds., McGraw-Hill, New York, 1998.

Thus, in one aspect the invention is useful whenever it is desirable to treat or prevent infection in a subject. This includes prophylactic treatment to prevent such infections in planned surgical procedures, as well as in emergency surgical situations, especially those involving intraabdominal surgeries. Intraabdominal surgeries include, for example, right hemicolectomy; left hemicolectomy; sigmoid colectomy; subtotal colectomy; total colectomy; cholecystectomy; gastrectomy; nephrectomy; vascular repair, including resection of abdominal aortic aneurysm; abscess drainage. Emergency surgeries include, in addition to any of the above, those to correct the following conditions: perforated ulcer (duodenal or gastric); perforated diverticulitis; obstructive diverticulitis; acute appendicitis; perforated appendicitis; blunt abdominal trauma; penetrating abdominal trauma; ruptured abdominal aorta, second operation to drain abscess; etc. The invention also is useful with non-intraabdominal surgeries such as orthopedic surgeries, pelvic and gynecologic surgeries, urologic surgeries, cardiothoracic surgeries, neurosurgeries, plastic and reconstructive surgeries, vascular surgeries, head and neck surgeries, and surgeries to correct wound infections. These listed surgeries are provided only by way of example and are not intended to be limiting.

A subject about to undergo surgery can be a subject scheduled to undergo an elective or non-emergency surgical procedure. Alternatively, a subject about to undergo surgery can be a subject about to have surgery on an emergency basis. Typically, a subject about to undergo surgery includes a subject that is to have a surgical procedure within the next 24 to 48 hours. A subject about to undergo surgery can include a subject that is to have a surgical procedure within the next 2 to 14 days.

A subject that has recently undergone surgery typically includes a subject that already had a surgical procedure in the previous 24 to 48 hours.

The antigens may be administered alone (e.g., in saline or buffer) or using any delivery vehicle known in the art. For instance, the following delivery vehicles have been described: cochleates (Gould-Fogerite et al., 1994, 1996); emulsomes (Vancott et al., 1998, Lowell et al., 1997); ISCOMs (Mowat et al., 1993, Carlsson et al., 1991, Hu et., 1998, Morein et al., 1999); liposomes (Childers et al., 1999, Michalek et al., 1989, 1992, de Haan 1995a, 1995b); live bacterial vectors (e.g., *Salmonella, Escherichia coli, Bacillus Calmette-Guerin, Shigella, Lactobacillus*) (Hone et al., 1996, Pouwels et al., 1998, Chatfield et al., 1993, Stover et al., 1991, Nugent et al., 1998); live viral vectors (e.g., Vaccinia, adenovirus, Herpes Simplex) (Gallichan et al., 1993, 1995, Moss et al., 1996, Nugent et al., 1998, Flexner et al., 1988, Morrow et al., 1999); microspheres (Gupta et al., 1998, Jones et al., 1996, Maloy et al., 1994, Moore et al., 1995, O'Hagan et al., 1994, Eldridge et al., 1989); nucleic acid vaccines (Fynan et al., 1993, Kuklin et al., 1997, Sasaki et al., 1998, Okada et al., 1997, Ishii et al., 1997); polymers (e.g., carboxymethylcellulose, chitosan) (Hamajima et al., 1998, Jabbal-Gill et al., 1998); polymer rings (Wyatt et al., 1998); Proteosomes (Vancott et al., 1998, Lowell et al., 1988, 1996, 1997); sodium fluoride (Hashi et al., 1998); transgenic plants (Tacket et al., 1998, Mason et al., 1998, Haq et al., 1995); virosomes (Gluck et al., 1992, Mengiardi et al., 1995, Cryz et al., 1998); virus-like particles (Jiang et al., 1999, Leibl et al., 1998). Those skilled in the art will recognize that other delivery vehicles that are known in the art may also be used.

The antigens can be used together with other therapeutic agents known in the art to be useful in treating particular conditions. When administered together with another therapeutic agent, the antigens can be administered before, with or after administration of the other therapeutic agent.

For example, the antigens can be administered in combination with anti-bacterial agents, anti-viral agents, anti-fungal agents, anti-mycobacterial agents, and anti-parasitic agents.

Anti-mycobacterials include quinolines such as 2-substituted-6,7-difluoro-3-methylquinoxaline 1,4-dioxides, clofazimine, *M. leprae* Hsp65-encoding plasmid DNA in biodegradable microparticles, azoles known to be inhibitors of cytochromes P450, 3-aryl-2-(1H-benzotriazol-1-yl)acrylonitriles, thiolactomycin analogues, sparfloxacin, benzoxazinorifamycins such as KRM-1648, rifampicin, phenothiazines, pyrazinamide, pro-drug ethionamide, and the like.

Anti-bacterial antibiotic drugs are well known and include, for example: amdinocillin, amikacin, aminoglycosides, amoxicillin, ampicillin, avlocillin, azithromycin, bacampicillin, carbenicillin, cefaclor, cefadoxil, cefamandole, cefazolin, cefmenoxine, cefonicid, cefoperazone, cefotaxime, cefotetan, cefoxitin, ceftazidme, ceftizoxime, ceftriaxone, cefuroxime axetil, cephalexin, cephradine, chloramphenicol, clavulanate, clindamycin, cloxacillin, cyclacillin, dicloxacillin, epicillin, erythromycin, flucloxacillin, gentamicin, hetacillin, imipenem, lincomycin, methicillin, metronidazole, mezlocillin, moxalactam, nafcillin, neomycin, oxacillin, penicillin G, penicillin V, piperacillin, pivampicillin, quinolones, rifampin, sulbactam, tetracyclines, ticarcillin, timentin, tobramycin, trimethoprim-sulfamethoxazole, and vancomycin. (See Goodman and Gilman's *The Pharmacological Basis of Therapeutics,* 9th Ed., 1996, McGraw Hill, Inc.)

Anti-virals include, for instance, but are not limited to acemannan; acyclovir; acyclovir sodium; adefovir; alovudine; alvircept sudotox; amantadine hydrochloride; aranotin; arildone; atevirdine mesylate; avridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscarnet sodium; fosfonet sodium; ganciclovir; ganciclovir sodium; idoxuridine; interferon alpha (IFN-α); kethoxal; lamivudine; lobucavir; memotine hydrochloride; methisazone; nevirapine; penciclovir; pirodavir; ribavirin; rimantadine hydrochloride; saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zidovudine; and zinviroxime.

Anti-fungals include, for instance, but are not limited to acrisorcin; ambruticin; amphotericin B; azaconazole; azaserine; basifungin; bifonazole; biphenamine hydrochloride; bispyrithione magsulfex; butoconazole nitrate; calcium undecylenate; candicidin; carbol-fuchsin; chlordantoin; ciclopirox; ciclopirox olamine; cilofungin; cisconazole; clotrimazole; cuprimyxin; denofungin; dipyrithione; doconazole; econazole; econazole nitrate; enilconazole; ethonam nitrate; fenticonazole nitrate; filipin; fluconazole; flucytosine; fungimycin; griseofulvin; hamycin; isoconazole; itraconazole; kalafungin; ketoconazole; lomofungin; lydimycin; mepartricin; miconazole; miconazole nitrate; monensin; monensin sodium; naftifine hydrochloride; neomycin undecylenate; nifuratel; nifurmerone; nitralamine hydrochloride; nystatin; octanoic acid; orconazole nitrate; oxiconazole nitrate; oxifungin hydrochloride; parconazole hydrochloride; partricin; potassium iodide; proclonol; pyrithione zinc; pyrrolnitrin; rutamycin; sanguinarium chloride; saperconazole; scopafungin; selenium sulfide; sinefungin; sulconazole nitrate; terbinafine; terconazole; thiram; ticlatone; tioconazole; tolciclate; tolindate; tolnaftate; triacetin; triafungin; undecylenic acid; viridofulvin; zinc undecylenate; and zinoconazole hydrochloride.

The antigens can be administered with anti-microbial antibodies such as but not limited to cytomegalovirus immune globulin, GAMIMUNE® N (Bayer), hepatitis B immune globulin, rabies immune globulin, and Varicella-Zoster immune globulin.

Figure 8A:
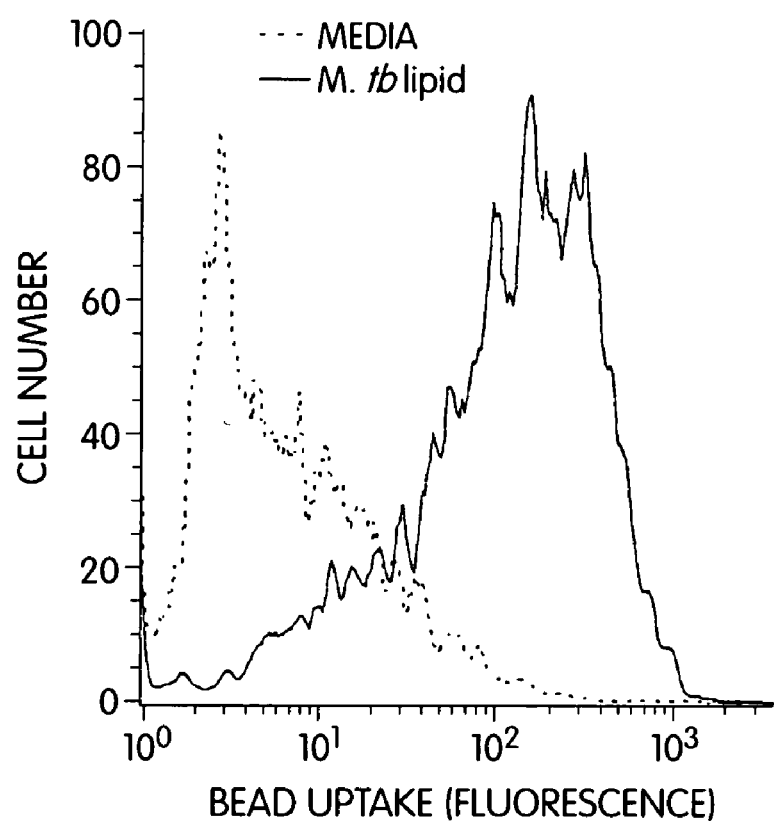
FIG. 8 shows the CD1a-restricted T cell response that occurs after co-administration of DDM and *M. tuberculosis* lipid adjuvants.
Figure 8B:
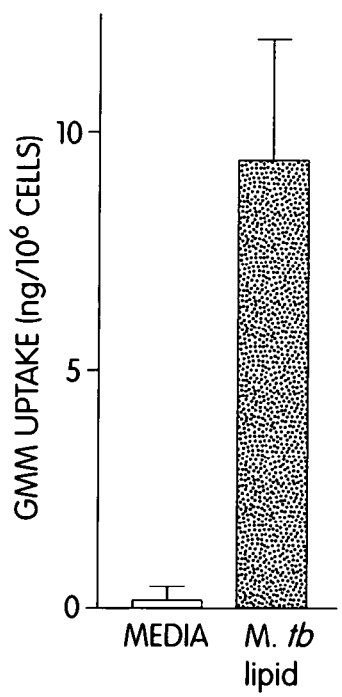
Figure 8C:
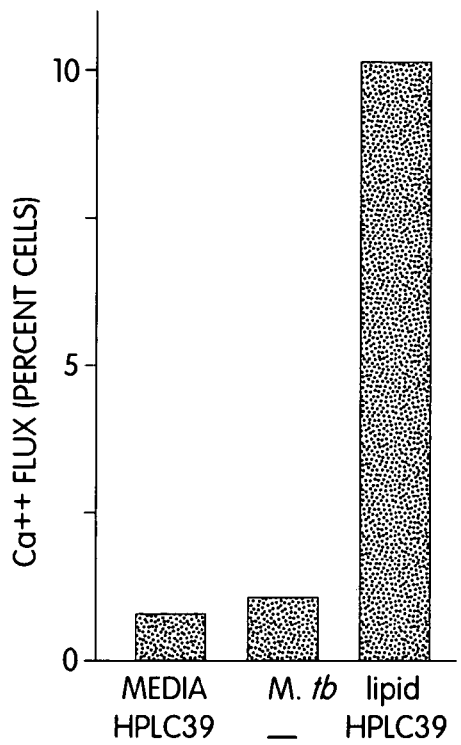

The antigens can also be administered with GM-CSF and IL-4 or crude mycobacterial wall preparations such as Freund's adjuvants or total lipid extracts from *M. tuberculosis* (FIG. 8).

Combined with the teachings provided herein, by choosing among the various antigens and their intended use, and weighing factors such as potency, relative bioavailability, patient body weight, severity of adverse side-effects and preferred mode of administration, an effective therapeutic treatment regimen can be planned which does not cause substantial toxicity and yet is entirely effective to treat the particular subject as described above. The effective amount for any particular application can vary depending on such factors as the disease or condition being treated, the particular antigen being administered, the size of the subject, or the severity of the disease or condition. One of ordinary skill in the art can empirically determine the effective amount of an antigen and/or other therapeutic agent without necessitating undue experimentation.

For adult human subjects, doses of the antigens typically range from about 50 µg/dose to 20 mg/dose, more typically from about 80 µg/dose to 8 mg/dose, and most typically from about 800 µg/dose to 4 mg/dose. Stated in terms of subject body weight, typical dosages range from about 0.5 to 500 µg/kg/dose, more typically from about 1 to 100 µg/kg/dose, and most typically from about 10 to 50 µg/kg/dose. Doses will depend on factors including the route of administration, e.g., oral administration may require a substantially larger dose than subcutaneous administration.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients. Compositions that comprise a pharmaceutically acceptable carrier are generally referred to herein as pharmaceutical compositions.

The pharmaceutical compositions of the invention contain a pharmaceutically-acceptable carrier. The term "pharmaceutically-acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the antigen, and with each other, in a manner such that there is no interaction which would substantially impair the desired pharmaceutical efficiency.

The antigens can be administered to a subject by any mode that delivers them to the desired site, e.g., mucosal, or they may be delivered systemically (e.g., parenteral). "Administering" the pharmaceutical composition of the present invention may be accomplished by any means known to the skilled artisan. The particular mode of administration selected will depend, of course, upon the particular adjuvants or antigen selected (depending upon the method employed), the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred routes of administration include but are not limited to oral, parenteral, intralesional, topical, transdermal, intramuscular, intranasal, intratracheal, inhalational, ocular, vaginal, and rectal.

For oral administration, the antigens and other agents can be formulated readily by combining with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the antigens may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The antigens, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the antigen may be in powder form for constitution with a suitable vehicle, e.g., sterile pyrogen-free water, before use.

The antigen may also be formulated in rectal or vaginal compositions such as suppositories or retention enemas, e.g., containing conventional suppository bases such as cocoa butter or other glycerides.

In addition to the formulations described previously, the antigen may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer *Science* 249:1527 (1990), which is incorporated herein by reference.

The antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulfuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2 percent w/v); citric acid and a salt (1-3 percent w/v); boric acid and a salt (0.5-2.5 percent w/v); and phosphoric acid and a salt (0.8-2 percent w/v). Suitable preservatives include benzalkonium chloride (0.003-0.03 percent w/v); chlorobutanol (0.3-0.9 percent w/v); parabens (0.01-0.25 percent w/v) and thimerosal (0.004-0.02 percent w/v).

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories. For treatment of a patient, depending on activity of the compound, manner of administration, purpose of the immunization (i.e., prophylactic or therapeutic), nature and severity of the disorder, age and body weight of the patient, different doses may be necessary. The administration of a given dose can be carried out both by single administration in the form of an individual dose unit or else several smaller dose units.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer-based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an antigen or other agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The identification and purification of a CD1a-presented antigen facilitates the identification of further antigens that bind to CD1a. One method provided by the invention is a screening method for other CD1a-presented antigens based on the ability of a compound to compete with, for example, DDM838 for binding to CD1a. Alternatively, variants of the disclosed antigens can be synthesized and tested for their ability to compete with binding of, for example, DDM838. Compounds so identified may be either agonists or antagonists, depending upon their effect on T cell stimulation following CD1a binding. If the compound is able to compete with DDM838 for binding to CD1a and then also activate CD1a restricted T cells, then the compound would be an agonist. If on the other hand it is able to compete with DDM838 but not activate CD1a restricted T cells, then it would be an antagonist. That is, the agonists and antagonists identified according to the invention are preferably identified by their ability to either substitute for or inhibit the effects of the CD1a -presented antigens of the invention.

Accordingly, the present invention further provides inhibitors of CD1a-restricted antigen presentation to T cells, i.e., CD1a blocking agents. CD1a antigen presentation can be inhibited by using a CD1a blocking agent to block the ability of a CD1a -restricted antigen to bind to CD1a . As used herein, a CD1a blocking agent is said to "inhibit CD1a-restricted antigen presentation" when the CD1a blocking agent decreases (1) the binding of a CD1a -presented antigen to a CD1a molecule or (2) the binding of a CD1a:CD1a-presented antigen complex to its cognate T cell receptors. Some CD1a blocking agents are able to block such binding to undetectable levels while other CD1a blocking agents only slightly decrease such binding. CD1a blocking agents include (1) agents which bind to CD1a, (2) agents which bind to the CD1a-presented antigen, (3) agents which bind to the CD1a:antigen complex, and (4) agents which bind to the T cell receptors that recognize the CD1a:antigen complex. Respective examples of blocking agents include, but are not limited to, (1) polyclonal or monoclonal antibodies which bind to and block the portion of a CD1a molecule that binds a CD1a-presented antigen, (2) polyclonal or monoclonal antibodies which bind to and block the portion of a CD1a-presented antigen that binds CD1a, (3) synthetic oligopeptides that are derived from the CD1a :antigen-binding portion of a T cell receptor and which bind to and block the portion of the CD1a:antigen complex bound by intact T cell receptors, and (4) synthetic compounds comprising a CD1a-presented antigen chemically linked to a purified CD1a molecule or a synthetic derivative thereof.

A skilled artisan can readily employ known methods of antibody generation, as well as rational blocking agent design in order to obtain the blocking agents of the present invention. Harlow, E., and Lane, D., Antibodies: A Laboratory Manual, Cold Spring Harbor Press, Cold Spring Harbor, 1988; Synthetic Peptides: Answers Guide, Freeman, W. H., New York, 1991; Kasprzak, A. A., Biochemistry 28:9230-9238 (1989). Additionally or alternatively, libraries of molecularly diverse molecules can be screened for individual member molecules which are CD1a blocking agents. Effective CD1a blocking agents are identified by their ability to inhibit CD1a-mediated T cell proliferative and/or cytolytic responses using the materials and methods described herein.

Standard binding assays are well known in the art, and a number of these are suitable in the present invention including ELISA, competition binding assay, sandwich assays, radioreceptor assays using radioactively labeled peptides or radiolabeled antibodies, immunoassays, etc. The nature of the assay is not essential provided it is sufficiently sensitive to detect binding of a small number of antigens.

A variety of other reagents also can be included in the binding mixture. These include reagents such as salts, buffers, neutral proteins (e.g., albumin), detergents, etc. which may be used to facilitate optimal binding. Such a reagent may also reduce non-specific or background interactions of the reaction components. Other reagents that improve the efficiency of the assay may also be used. The mixture of the foregoing assay materials is incubated under conditions may mimic physiological conditions, but is not so limited. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours. After incubation, the presence or absence of specific binding between the agent and the antigen, antigen/CD1a complex, or antigen/CD1a/TCR complex is detected by any convenient method available to the user.

Typically, a plurality of assay mixtures are run in parallel with differing concentrations of antigen (or complex) to obtain a different response to the various concentrations. One of these concentrations serves as a negative control, i.e., at zero concentration of antigen or complex or at a concentration below the limits of assay detection.

A separation step is often used to separate bound from unbound agent. The separation step may be accomplished in a variety of ways. Conveniently, at least one of the components (e.g., peptide or antibody) is immobilized on a solid substrate via binding to the antigen or complex. The unbound components may be easily separated from the bound fraction. The solid substrate can be made of a wide variety of materials and in a wide variety of shapes, e.g., columns or gels of polyacrylamide, agarose or sepharose, microtiter plates, microbeads, resin particles, etc. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

The invention further provides diagnosis or detection methods for determining whether a sample contains one of more of the antigens of the invention. The sample may be from a subject and may include but is not limited to sputum, semen, blood, saliva, joint fluid, and the like. It may be harvested by biopsy or other form of extraction but it is not so limited. The method involves contacting such a sample with an agent that binds to one or more of the antigens of the invention. The agent may is generally a binding partner of the antigen. It may include binding peptides or proteins such as but not limited to antibodies and fragments thereof. The agent may be directly or indirectly labeled with a detectable moiety in order to visualize and preferably quantitate the amount of antigen in the sample. A detectable label is a moiety, the presence of which can be ascertained directly or indirectly. Generally, detection of the label involves an emission of energy by the label. The label can be detected directly by its ability to emit and/or absorb light of a particular wavelength. A label can be detected indirectly by its ability to bind, recruit and, in some cases, cleave another moiety which itself may emit or absorb light of a particular wavelength. An example of indirect detection is the use of a first enzyme label which cleaves a substrate into visible products. The label may be of a chemical, peptide or nucleic acid nature although it is not so limited. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin and enzyme tags such as horseradish peroxidase, $\beta$-galactosidase, etc.

The method preferably includes a comparison of the binding levels of the sample to one or more controls. The controls may be positive or negative controls or both. The controls may be samples of known content that are run at the same time as the test sample, or they may be standard curves on which the test data is plotted.

The agent may be an antibody. An antibody, as is well known in the art, is an assembly of polypeptide chains linked by disulfide bridges. Two principle polypeptide chains, referred to as the light chain and heavy chain, make up all major structural classes (isotypes) of antibody. Both heavy chains and light chains are further divided into subregions referred to as variable regions and constant regions. In some instances, the peptides encompass the antibody heavy and light variable chains of the foregoing antibodies. The heavy chain variable region is a peptide which generally ranges from 100 to 150 amino acids in length. The light chain variable region is a peptide which generally ranges from 80 to 130 amino acids in length.

As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions of the antibody, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. An isolated F(ab')$_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')$_2$ and Fv are employed with either standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford)].

The agent may be an antibody fragment or a binding peptide. Such fragments and peptides may encompass the complementarity determining regions (i.e., CDRs) of the foregoing variable regions. As is well-known in the art, CDRs of an antibody are the portions of the antibody which are largely responsible for antibody specificity. The CDRs directly interact with the epitope of the antigen (see, in general, Clark, 1986; Roitt, 1991). In both the heavy chain and the light chain variable regions of IgG immunoglobulins, there are four framework regions (FR1 through FR4) separated respectively by three complementarity determining regions (CDR1, CDR 2 and CDR3). The framework regions (FRs) maintain the tertiary structure of the paratope, which is the portion of the antibody which is involved in the interaction with the antigen. CDRs, and in particular CDR3, and more particularly heavy chain CDR3, contribute to antibody specificity. Because CDRs, and in particular CDR3, confer antigen specificity on the antibody, these regions may be incorporated into other antibodies or peptides to confer the identical antigen specificity onto that antibody or peptide.

The invention embraces antibodies that bind to the antigens of the invention as therapeutic or diagnostic agents. The antibodies may be either monoclonal antibodies or polyclonal antibodies. One of ordinary skill in the art will be familiar with polyclonal antibody preparation. Briefly, this involves intradermal administration of an antigen with an adjuvant such as but not limited to Freund's complete adjuvant into for example an animal (e.g., a mouse or a rabbit). Approximately one month later, the animals are boosted with ⅕-1/10 of the original amount of antigen in adjuvant by subcutaneous injection at multiple sites. One to two weeks later the animals are bled, and the serum is assayed for the presence of antibody. The animals may be repeatedly boosted until the antibody titer plateaus.

In addition to supplying a source of polyclonal antibodies, the immunized animals can be used to generate monoclonal antibodies. As used herein, the term "monoclonal antibody" refers to a homogenous population of immunoglobulins that bind to the same epitope (i.e., antigenic determinant). Monoclonal antibodies have the same Ig gene rearrangement and thus demonstrate identical binding specificity. Monoclonal antibodies can be prepared by any method known in the art such as by immortalizing spleen cells isolated from the immunized animal by e.g., fusion with myeloma cells or by Epstein Barr Virus transformation, and screening for clones expressing the desired antibody. Other methods involve isolation of rearranged Ig gene sequences and cloning into immortalized cell lines. Methods for preparing and using monoclonal antibodies are well known in the art. The following description of a method for developing an monoclonal antibody is exemplary and is provided for illustrative purposes only. Balb/c mice are immunized intraperitoneally with approximately 75-100 µg of purified antigen in complete Freund's adjuvant. Booster injections of approximately 25-50 µg antigen in incomplete Freund's are administered on approximately days 15 and 35 after the initial injection. On day 60-65, the mice receive booster injections of approximately 25 µg antigen in the absence of adjuvant. Three days later, the mice are killed and the isolated spleen cells fused to murine myeloma NS-1 cells using polyethylene glycol by a procedure such as that described by Oi (Oi VT: Immunoglobulin-producing hybrid cell lines in Herzenberg LA (ed): Selected Methods in Cellular Biology, San Francisco, Calif., Freeman, (1980)). Hybridoma cells are selected using hypoxanthine, aminopterin, and thymidine (HAT) and grown in culture. Fourteen to fifteen days after fusion, hybridoma cells producing monoclonal antibodies are identified using a solid-phase radioimmunoassay by capturing antigen-specific antibodies from conditioned media with immobilized goat anti-mouse IgG. Hybridomas testing positive for antibodies against the antigen are subcloned by limiting dilution and re-tested. Ascites for the hybridomas is then prepared in pristane-primed BALB/c mice by injecting approximately 1×10$^6$ cells/mouse. Concentrates enriched in the selected monoclonal antibodies are produced from ascites fluid by gel filtration on S-200 and concentrated with NH$_4$SO$_4$. The pellets are dissolved in an appropriate storage solution such as 50% glycerol/H$_2$O and are stored at 4° C.

Isolated antibodies as used herein refer to antibodies that are substantially physically separated from other cellular material (e.g., separated from cells which produce the antibodies) or from other material that hinders their use either in the diagnostic or therapeutic methods of the invention.

Preferably, the isolated antibodies are present in a homogenous population of antibodies (e.g., a population of monoclonal antibodies). Compositions of isolated antibodies can however be combined with other components such as but not limited to pharmaceutically acceptable carriers, adjuvants, and the like.

Isolated antibody producing cells including isolated hybridomas and isolated recombinant cells, as used herein, refer to antibody-producing cells that are substantially physically separated from other cells, other bodily material (e.g., ascites tissue and fluid), and other material that hinders their use in the production of for example an isolated and preferably homogenous antibody population.

The invention further contemplates humanized antibodies and antibody fragments. A "humanized monoclonal antibody" as used herein is a human monoclonal antibody or functionally active fragment thereof having at least human constant regions and an antigen binding region (e.g., a CDR) from a mammal of a species other than a human. An intact humanized monoclonal antibody in an isolated form or in a pharmaceutical preparation is particularly suited to some aspects of the invention. Humanized antibodies have particular clinical utility in that they specifically recognize antigens, but will not evoke an immune response in humans against the antibody itself. In one preferred embodiment, a murine CDR is grafted into the framework region of a human antibody to prepare the "humanized antibody." See, e.g., L. Riechmann et al., Nature 332, 323 (1988); M. S. Neuberger et al., Nature 314, 268 (1985) and EPA 0 239 400 (published Sep. 30, 1987).

Human monoclonal antibodies may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51-63 (Marcel Dekker, Inc, New York, 1987), and Boerner et al., *J. Immunol.*, 147: 86-95 (1991). In addition to the conventional methods for preparing human monoclonal antibodies, such antibodies may also be prepared by immunizing transgenic animals that are capable of producing human antibodies (e.g., Jakobovits et al., *PNAS USA*, 90: 2551 (1993), Jakobovits et al., *Nature*, 362: 255-258 (1993), Bruggermann et al., *Year in Immunol.*, 7:33 (1993) and U.S. Pat. No. 5,569,825 issued to Lonberg). There are entities in the United States which will synthesize humanized antibodies from specific murine antibody regions commercially, such as Protein Design Labs (Mountain View Calif.), Abgenix, and Medarex.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Antigen identification and isolation has been described supra.

Figure 5:
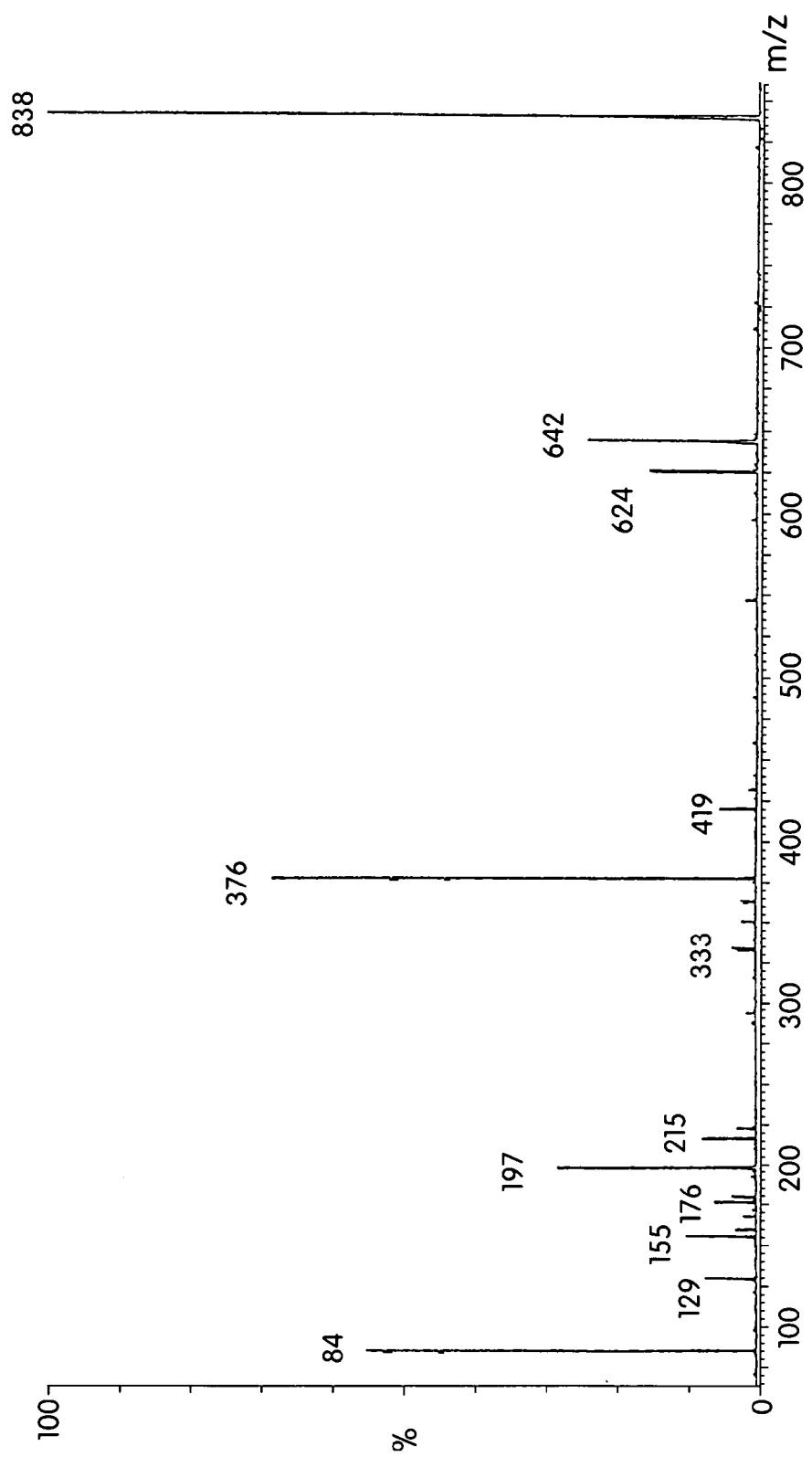

The positive ion mode electrospray ionization mass spectrum (MS/MS) of *M. tuberculosis* DDM838 is illustrated in FIG. 5. The MH+ ion with a nominal mass to charge ratio of 838 yields product ions consistent with the known depicted structure of 838 shown in the lower panel of FIG. 9.

Fourier transform ion cyclotron resonance mass spectrometry (FTICR-MS) demonstrated the MH$^+$ to be m/z 838.5684, matching the value calculated for $C_{47}H_{76}N_5O_8$ (838.5688). Tandem mass spectrometry (MS/MS) yielded product ions at m/z 642 and m/z 197, which were each 16 u (the mass of oxygen) smaller than the previously described mycobactic acid and cobactin fragments of mycobactin, a known mycobacterial lipopeptide with iron scavenging properties (G. A. Snow, *Bacteriol. Rev.* 34, 99 (1970), J. Gobin et al., *Proc. Natl. Acad. Sci. U.S.A.* 92, 5189 (1995). Therefore, the antigen was named didehydroxymycobactin (DDM838). Identification of MS/MS products at m/z 727 and 84 indicates that the hydroxylysines found in mycobactin were substituted by lysines in the proposed structure for DDM (J. Gobin et al., *Proc. Natl. Acad. Sci. U.S.A.* 92, 5189 (1995). The presence of lysine in DDM was confirmed by gas chromatography-mass spectrometry (GC-MS) of acid hydrolysis products. Unexpectedly, GC-MS detected an uncommon amino acid, α-methyl serine, instead of serine and threonine, which are present in most mycobacterial mycobactins (D. B. Moody et al., unpublished observations; G. A. Snow, *Bacteriol. Rev.* 34, 99 (1970); M. Tsukamoto et al., *J. Antibiot* (Tokyo) 50, 815 (1997). The identity of α-methyl serine as a component of DDM was confirmed by the nuclear magnetic resonance (NMR) spectrum of DDM.

Figure 9:
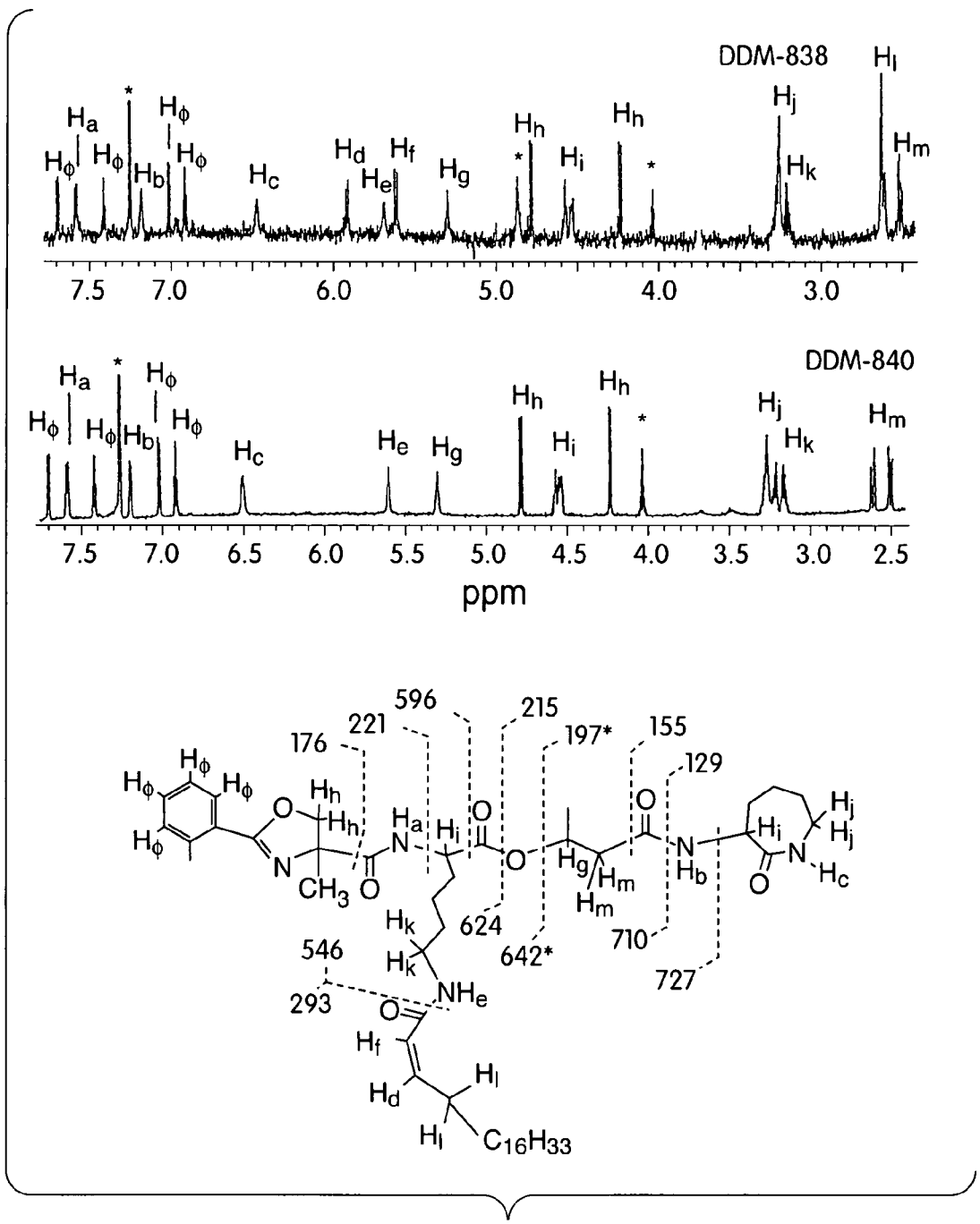
FIG. 9 is a graph showing proton nuclear magnetic resonance spectra of DDM838 and DDM840 (upper panels) and proton assignments (lower panel).

Downfield regions of one-dimensional proton NMR spectra of DMM-838 (upper) and DDM840 (lower) show resonances that are assigned as aromatic ($H_{\Phi}$) or other protons (Ha-n) (FIG. 9). The olefinic protons $H_d$ and $H_f$ are present in DDM838, but not in DDM840, and are coupled to each other with a J constant of 12.1 Hz. This is consistent with a double bond, which is likely present at $C_{2-3}$, because the doublet corresponding to $H_f$ is directly coupled to only one proton, $H_d$ $H_d$ is directly coupled to the two $H_l$ and is shifted downfield of its olefinic partner, Hf, as expected for a C=C—C=O system. Further supporting this conclusion, $H_k$ protons were also shifted slightly for DDM838 relative to DDM840 as a result of the influence of the olefin, which provides evidence for conjugation with the carboxyl group. The identification of α-methyl serine was based in part on the observations that $H_h$ protons are only split by each other, suggesting that they are geminal protons in an oxazoline ring adjacent to a quaternary carbon. The acyl chain gave a typical terminal methyl triplet at 0.880 parts per million (ppm) and a large signal centered at 1.257 ppm, which obscures the signal from the methyl protons of the methyl serine associated with the oxazoline ring. Two obvious impurity peaks (6.97 and 3.775 ppm, upper panel), as well as spinning sidebands from the CHCL3, have been deleted for clarity. Unassigned resonances, probably impurities, are denoted with an asterisk. Two-dimensional $^1$H-$^1$H data were also obtained and corroborate all implied adjacent proton relations (not shown).

Figure 2:
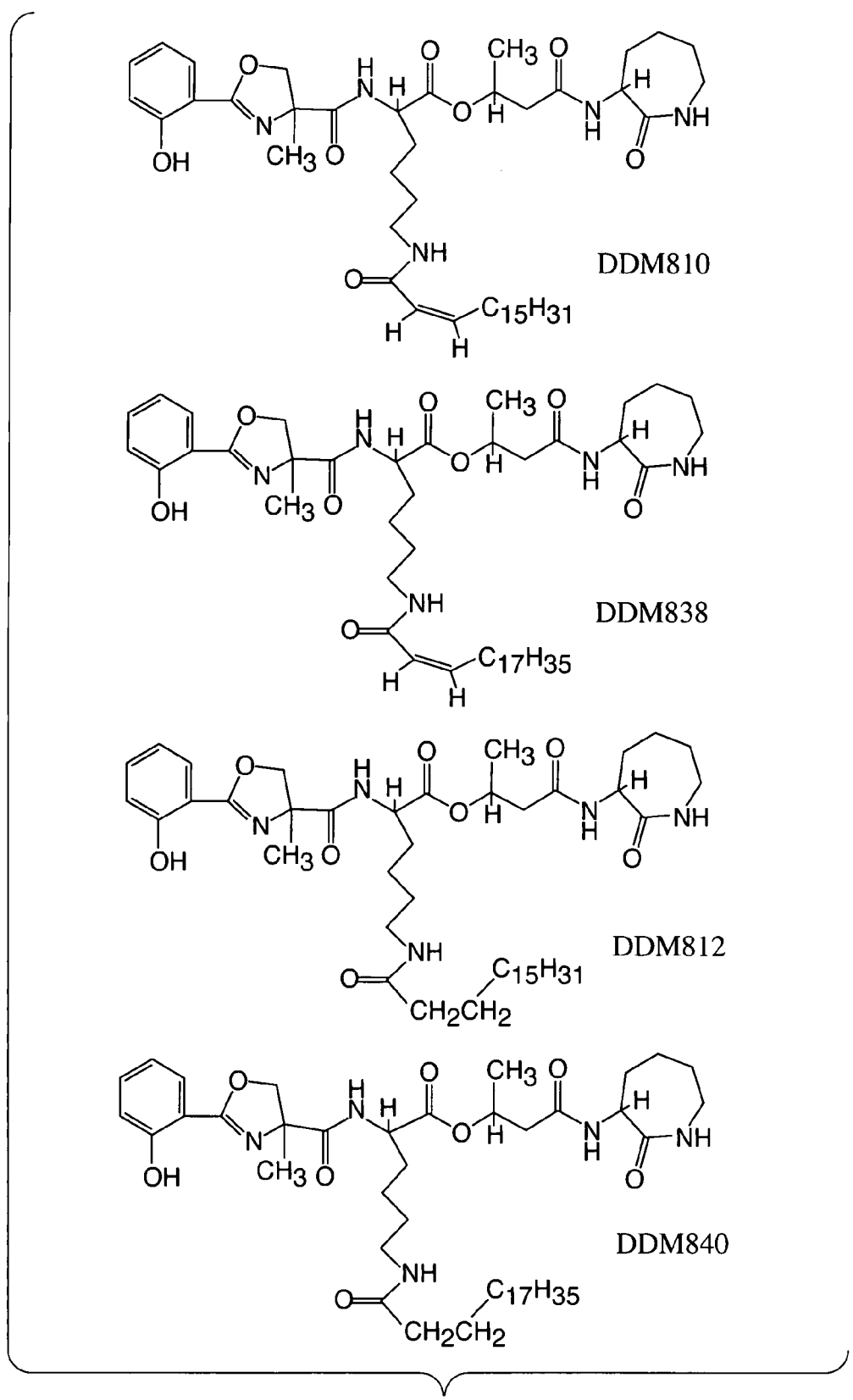

These studies establish the structure of one category of CD1a-presented antigens produced by *M. tuberculosis* and show that they conform to a general structure in FIG. 1, which is composed of salicylic acid, α-methyl serine, acylated lysine, hydroxybutyrate, and cyclized lysine (FIGS. 1, 2 and 9).

T cell activation assays were carried out as follows. CD1-restricted T cells were incubated in the presence of purified antigen DDM838 and the proliferation index was measured in terms of incorporation of radioactivity (cpm). As an example, T cells ($5\times10^4$) and irradiated (5000 rads) CD1+ monocytes ($5\times10^4$) as APCs were cultured in 96 well flat-bottom plates in the presence of antigen. Cultures were collected on days 3 or 4, after a 6 hour pulse with 1 μCi/well

[³H]thymidine (New England Nuclear, Boston, Mass.) and [³H]thymidine incorporation was determined by liquid scintillation counting.

FIG. 6 shows the activation of J.RT-3 T lymphoblastoid cells in response to *M. tuberculosis* lipid fractions that contain DDM838. J.RT-3 cells transfected with the T cell receptor alpha and beta chains from the CD8-2 T cell line cells were assessed for activation in response to C1R B lymphoblastoid cells transfected with the indicated CD1 isoform and antigen preparations (Ag) made from *M. tuberculosis* lipid fractions containing DDM838. Activation was measured by calcium flux, as assessed by changes in the fluorescence properties of the Ca-dependent fluorophores Fura Red and Fluo-4 in flow cytometric experiments. Strong calcium flux was seen when DMM838 (Ag) was added to C1R cells transfected with CD1a proteins and J.RT-3 cells were transfected with the CD8-2 T cell receptor (TCR) chains. No activation was seen when antigen, TCR or CD1a were omitted, or when the cells were not briefly subjected to centrifugation (spin) to initiate contact between cells.

FIG. 7 shows the response of CD1a-restricted T cell lines to natural homologs of *M. tuberculosis* DDM antigens. Interleukin-2 (IL-2) release of J.RT-3/CD8-2 cells was measured using a bioassay that measures IL-2 dependent proliferation of HT-2 T cells. Using reversed phase high performance liquid chromatography, DDM810, DDM812, DDM838 and DDM840 were purified to homogeneity as determined by positive mode electrospray ionization mass spectrometry. Each compound was added to C1R B lymphoblastoid cells expressing CD1a proteins at the indicated dose and IL-2 was measured after 24 hours of co-culture.

FIG. 8 shows that co-administration of DDM and *M. tuberculosis* lipid adjuvants leads to a CD1a-restricted T cell response. The assay uses HPLC 39 which is a lipid fraction that contains DMM838. The Figure shows that DDMs can be added together with adjuvants (such as *M. tuberculosis* total lipids) to give a T cell response. Monocytes were cultured for 3 days in media alone (dashed) or M. tb lipid adjuvant (solid line, 10 μg/ml) and then incubated with FITC-labeled dextran for 2 hours, washed and analyzed by flow cytometry. Alternatively, monocytes were incubated with [¹⁴C]-labeled $C_{32}$ GMM for 6 hours, washed and subjected to scintillation counting to measure total cell-associated GMM. Monocytes were treated with media or M. tb lipids (10 μg/ml), washed and then cultured with an M. tb lipid fraction containing DDM838 (HPLC 39) overnight. These cells were washed to remove antigen and mixed with J.RT-3/CD8.2 cells and subjected to flow cytometric analysis for calcium flux. The results show that CD1a-presented lipid antigens are more stimulatory (e.g., perhaps by being presented more efficiently) when myeloid APCs are treated with adjuvant. DDM838 was not above to activate polyclonal T cells or CD1b or CD1c transfectants, indicating that the observed T cell response was not due to mitogen effects.

EQUIVALENTS

Each of the foregoing patents, patent applications and references recited in this application is incorporated herein in its entirety by reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

We claim:
1. An isolated compound of Formula 1, wherein Formula I is

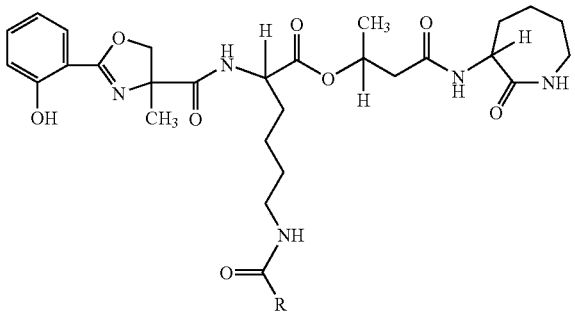

wherein R is an alkyl chain or an alkene chain.

2. The isolated compound of claim 1, wherein the isolated compound has a structure of Formula II

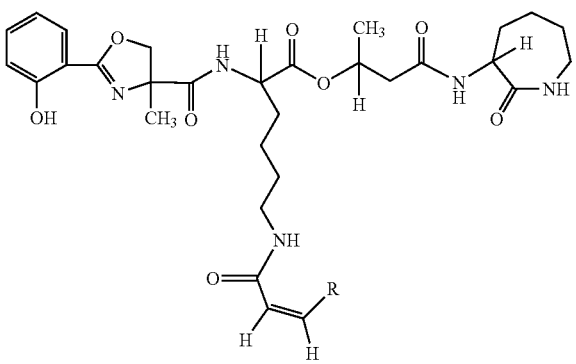

wherein R is an alkyl chain or an alkene chain.

3. The isolated compound of claim 1, wherein the isolated compound has a structure of Formula III

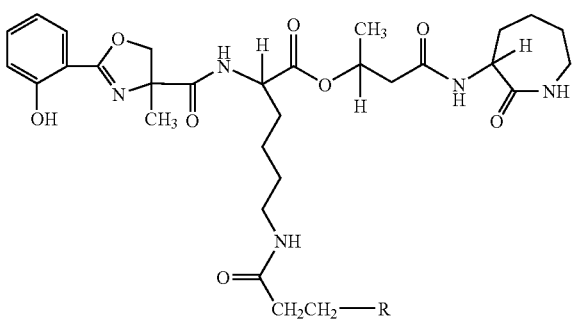

wherein R is an alkyl chain or an alkene chain.

4. The isolated compound of claim 1, wherein the isolated compound is

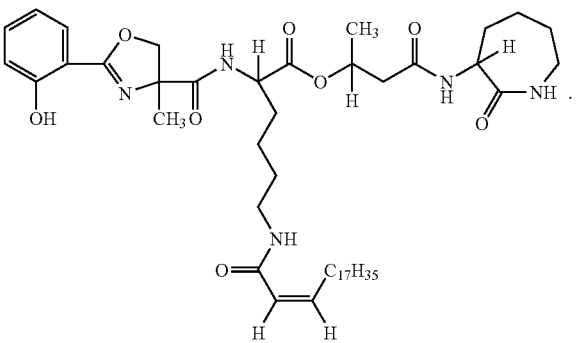

5. The isolated compound of claim 1, wherein the isolated compound is

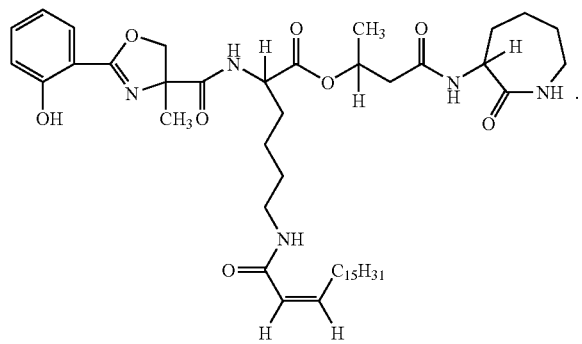

6. The isolated compound of claim 1, wherein the isolated compound is

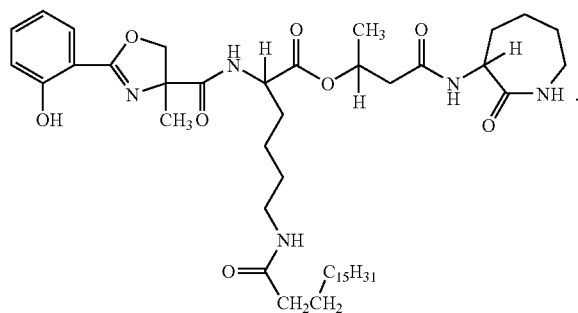

7. The isolated compound of claim 1, wherein the isolated compound is

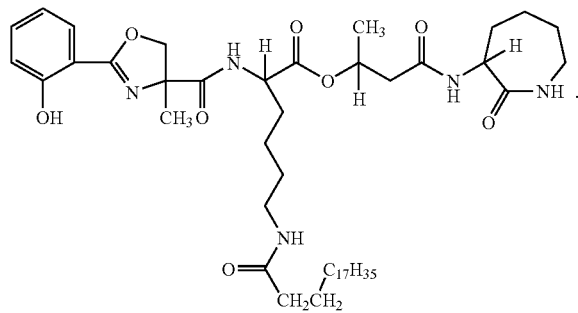

8. An isolated compound of Formula IV, wherein Formula IV is

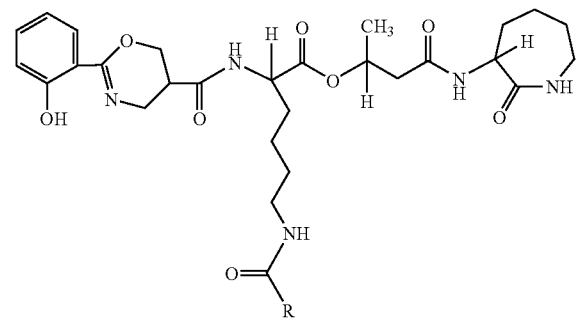

wherein R is an alkyl chain or an alkene chain.

9. A pharmaceutical composition comprising an effective amount of the compound of claim 1, and a pharmaceutically acceptable carrier.

10. The isolated compound of claim 2, wherein R is at least 17 carbons in length.

11. The isolated compound of claim 2, wherein R is selected from the group consisting of C20, C20:1, C19, C19:1, C18 and C18:1.

12. The isolated compound of claim 2, wherein R is selected from the group consisting of C20:1, C19:1, C18:1 and C17:1.

13. The isolated compound of claim 2, wherein R is an alkene chain.

14. The isolated compound of claim 1, wherein the isolated compound is present on a CD1a-expressing cell.

15. The isolated compound of claim 14, wherein the CD1a-expressing cell is a dendritic cell.

16. The isolated compound of claim 14, wherein the CD1a-expressing cell is a transfected cell.

17. The isolated compound of claim 14, wherein the CD1a-expressing cell is a cell cultured in GM-CSF and IL-4.

18. A method for isolating a compound of Formula I wherein Formula I is

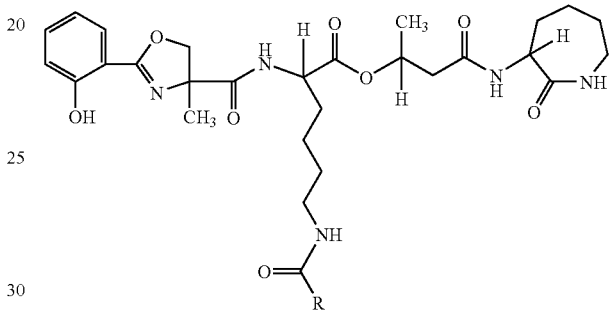

wherein R is of an alkyl chain or an alkene chain, comprising
performing a cold acetone precipitation of a mycobacterial sample to form a precipitate,
dissolving the precipitate in chloroform,
eluting the dissolved precipitate through a silica gel in a methanol solvent, and
performing a reversed phase HPLC using C8 matrix.

19. A method for isolating a compound of Formula IV wherein Formula IV is

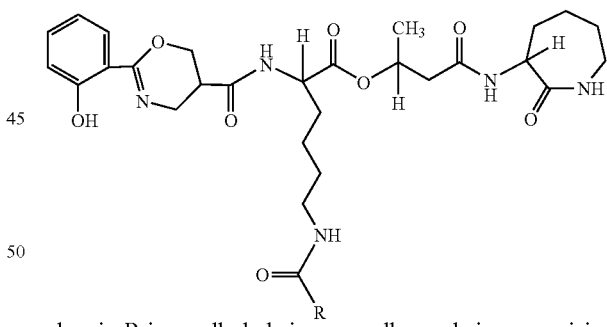

wherein R is an alkyl chain or an alkene chain, comprising

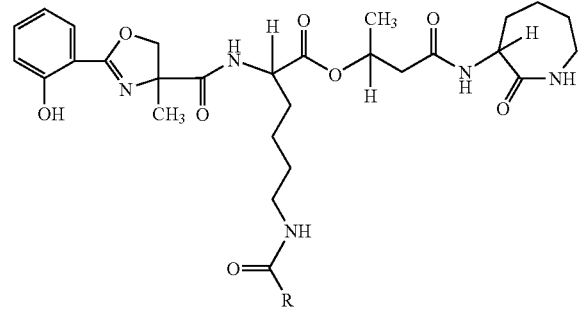

wherein R is an alkyl chain or an alkene chain.

20. A pharmaceutical composition comprising an effective amount of the isolated compound of claim 8, and a pharmaceutically acceptable carrier.

21. The isolated compound of claim 8, wherein the isolated compound is

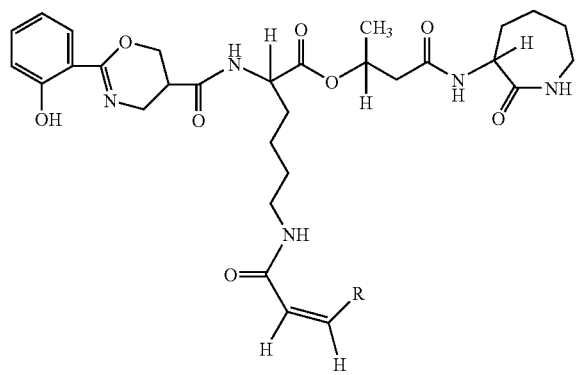

wherein R is an alkyl chain or an alkene chain.

22. The isolated compound of claim 8, wherein the isolated compound is

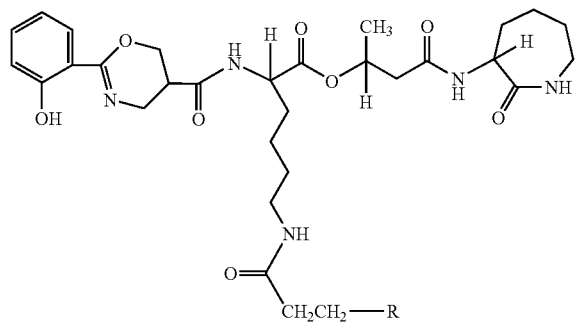

wherein R is an alkyl chain or an alkene chain.

23. The isolated compound of claim 21, wherein R is $C_{15}H_{31}$ or $C_{17}H_{35}$.

24. The isolated compound of claim 22, wherein R is $C_{15}H_{31}$ or $C_{17}H_{35}$.

25. The isolated compound of claim 3, wherein R is selected from the group consisting of C20, C20:1, C19, C19:1, C18 and C18:1.

26. The isolated compound of claim 3, wherein R is selected from the group consisting of C20:1, C19:1, C18:1 and C17:1.

27. The isolated compound of claim 8, wherein R is selected from the group consisting of C20, C20:1, C19, C19:1, C18 and C18:1.

28. The isolated compound of claim 8, wherein R is selected from the group consisting of C20:1, C19:1, C18:1 and C17:1.

29. The method of claim 18, wherein the antigen is DDM838

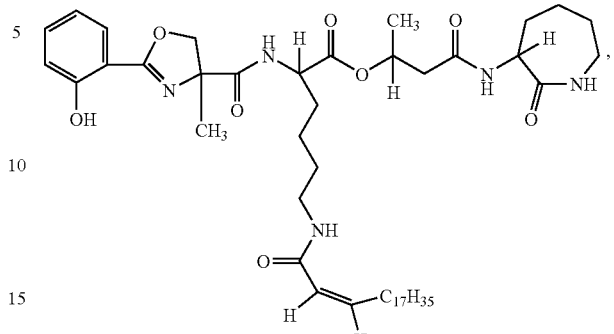

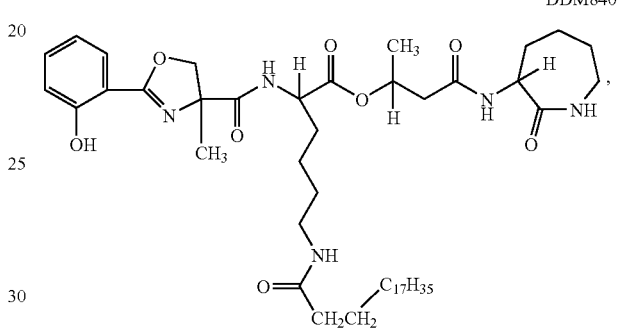

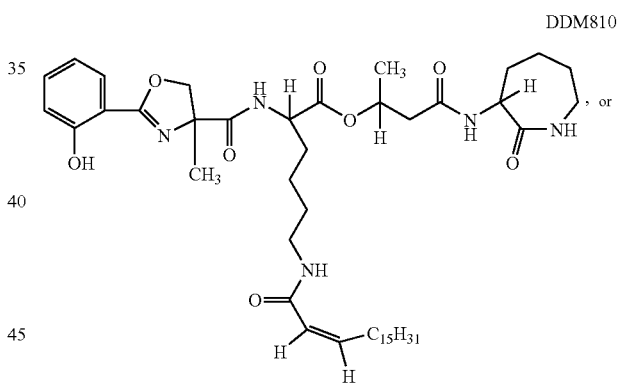

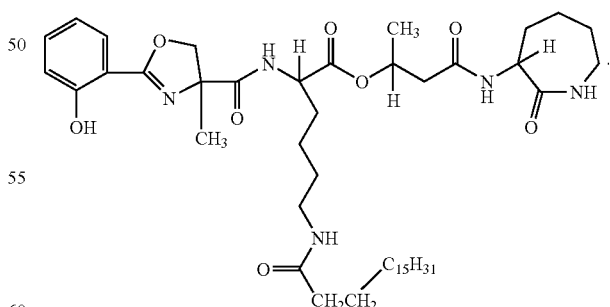

30. The method of claim 18, wherein the mycobacterial sample is a *M. tuberculosis* sample.

31. The method of claim 19, wherein the mycobacterial sample is a *M. tuberculosis* sample.

32. The method of claim 19, wherein the antigen is DDM838-threonine
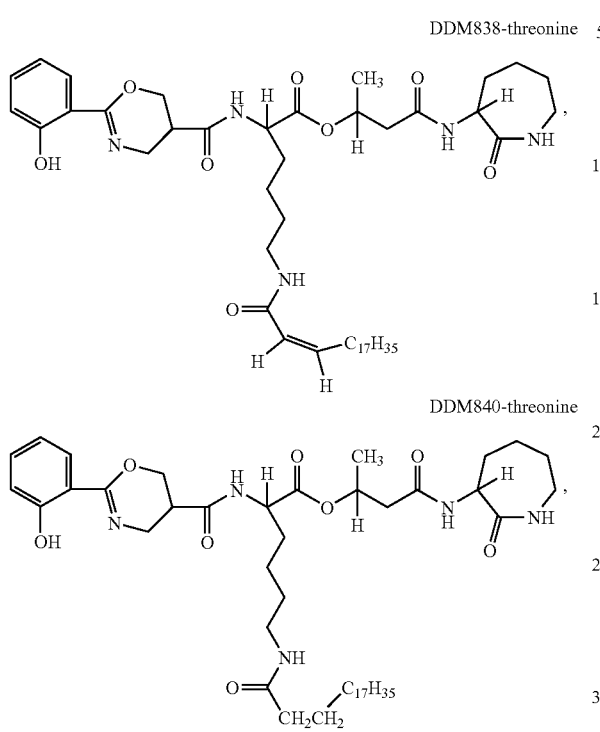
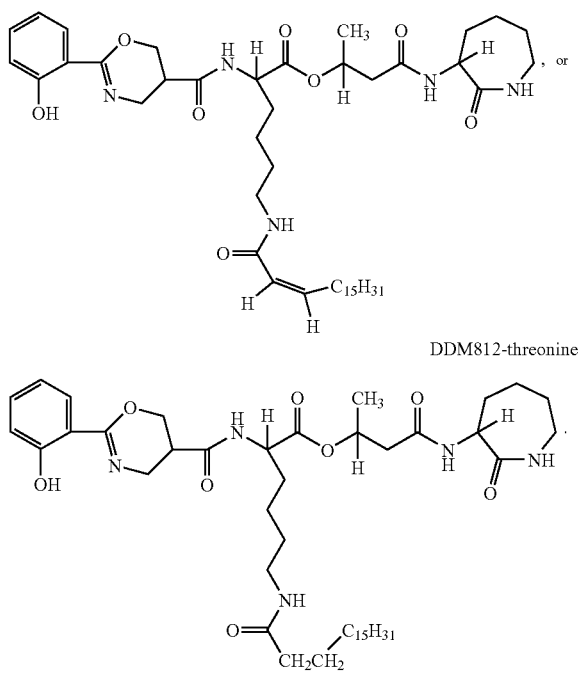
* * * * *

UNITED STATES PATENT AND TRADEMARK OFFICE
CERTIFICATE OF CORRECTION

PATENT NO. : 7,253,159 B2  Page 1 of 1
APPLICATION NO. : 10/827616
DATED : August 7, 2007
INVENTOR(S) : D. Branch Moody et al.

It is certified that error appears in the above-identified patent and that said Letters Patent is hereby corrected as shown below:

In Claim 18, column 38, line 32, delete "wherein R is of an alkyl" and insert -- wherein R is an alkyl", In Claim 19, column 38, line 54, delete the structure that is duplicated and the second recitation of "wherein R is an alkyl chain or an alkene chain" and insert the following after the first recitation of the word "comprising"

--performing a cold acetone precipitation of a mycobacterial sample to form a precipitate,
dissolving the precipitate in chloroform,
eluting the dissolved precipitate through a silica gel in a methanol solvent, and
performing a reversed phase HPLC using C8 matrix.--.

In Claim 29, column 40, line 2, delete the first recitation of "DDM838".

In Claim 32, column 41, line 2, delete the first recitation of "DDM838-threonine".

Signed and Sealed this

Thirteenth Day of November, 2007

JON W. DUDAS
*Director of the United States Patent and Trademark Office*